US008450059B2

(12) United States Patent
Fredricks et al.

(10) Patent No.: US 8,450,059 B2
(45) Date of Patent: May 28, 2013

(54) QUANTITATIVE PCR-BASED COMPOSITIONS AND METHODS FOR THE DIAGNOSIS OF INVASIVE PULMONARY ASPERGILLOSIS

(75) Inventors: David N. Fredricks, Seattle, WA (US); Prasanna D. Khot, Cottonwood Heights, UT (US); Daisy L. Ko, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 320 days.

(21) Appl. No.: 12/768,632

(22) Filed: Apr. 27, 2010

(65) Prior Publication Data

US 2010/0273169 A1  Oct. 28, 2010

Related U.S. Application Data

(60) Provisional application No. 61/173,065, filed on Apr. 27, 2009.

(51) Int. Cl.
*C12Q 1/68* (2006.01)
*C07H 21/04* (2006.01)

(52) U.S. Cl.
USPC .......................... 435/6.1; 435/975; 536/24.33

(58) Field of Classification Search
None
See application file for complete search history.

(56) References Cited

PUBLICATIONS

Yamakami et al. (J Clin Microbiol. Oct. 1996;34(10):2464-8).*
Kobayashi et al. (Intern Med. Jul. 1999;38(7):563-9).*
NCBI Genbank Accession No. AB008401 (Feb. 13, 1999).*
Buck et al ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Adam, O., et al.; "Treatment with piperacillin-tazobactam and false-positive *Aspergillus galactomannan* antigen test results for patients with hematological malignancies," Clin Infect Dis, vol. 38, pp. 917-920, 2004.
Wages, J., et al.; "Removal of contaminating DNA from PCR reagents by ultrafiltration," Biotechniques, vol. 16, pp. 1014-1017, 1994.
Ascioglu, S., et al. ; "Defining opportunistic invasive fungal infections in immunocompromised patients with cancer and hematopoietic stem cell transplants: an international consensus," Clin Infect Dis, vol. 34, pp. 7-14, 2002.
Bretagne, S., et al. ; "Detection of *Aspergillus* species DNA in bronchoalveolar lavage samples by competitive PCR," J Clin Microbiol, vol. 33, pp. 1164-1168, 1995.
Bretagne, S.; "Molecular diagnostics in clinical parasitology and mycology: limits of the current polymerase chain reaction (PCR) assays and interrest of the real-time PCR assays," Clin Microbiol Infect, vol. 9, pp. 505-511, 2003.
Buchheidt, D., et al.; "Detection of *Aspergillus* species in blood and bronchoalveolar lavage samples from immunocompromised patients by means of 2-step polymerase chain reaction: clinical results," Clin Infect Dis, vol. 33, pp. 428-435, 2001.
Caliendo, A.; "Performance of a PCR assay for detection of *Pneumocystis carinii* from respiratory specimens," J Clin Microbiol, vol. 36, pp. 979-982, 1998.
Ferns, R.; "Evaluation of the role of real-time PCR in the diagnosis of invasive aspergillosis," Leuk Lymphoma, vol. 47, pp. 15-20, 2006.
Griffiths, L., et al.; "Comparison of DNA extraction methods for *Aspergillus fumigatus* using real-time PCR," J Med Microbiol, vol. 55, pp. 1187-1191, 2006.
Hayette, M., et al. ; "Detection of *Aspergillus* species DNA by PCR in bronchoalveolar lavage fluid," J Clin Microbiol, vol. 39, pp. 2338-2340, 2001.
Herbrecht, R., et al.; "*Aspergillus galactomannan* detection in the diagnosis of invasive aspergillosis in cancer patients," J Clin Oncol, vol. 20, pp. 1898-1906, 2002.
Hoorfar, J., et al.; "Practical considerations in design of internal amplification controls for diagnostic PCR assays," J Clin Microbiol, vol. 42, pp. 1863-1868, 2004.
Jordan, J., et al.; "Comparison of 16S rRNA gene PCR and BACTEC 9240 for detection of neonatal bacteremia," J Clin Microbiol, vol. 38, pp. 2574-2578, 2000.
Kedzierska, A., et al.; "Current status of fungal cell wall components in the immunodiagnostics of invasive fungal infections in humans: galactomannan, mannan and (1—>3)-beta-D-glucan antigens," Eur J Clin Microbiol Infect Dis, vol. 26, pp. 755-766, 2007.
Latge, J.; "*Aspergillus fumigatus* and aspergillosis," Clin Microbiol Rev, vol. 12, pp. 310-350, 1999.
Levy, H., et al.; "The value of bronchoalveolar lavage and bronchial washings in the diagnosis of invasive pulmonary aspergillosis," Respir Med, vol. 86, pp. 243-248, 1992.
Limaye, A., et al.; "Cytomegalovirus (CMV) DNA load in plasma for the diagnosis of CMV disease before engraftment in hematopoietic stem-cell transplant recipients," J Infect Dis, vol. 183, pp. 377-382, 2001.
Loeffler, J., et al.; "Contaminations occurring in fungal PCR assays," J Clin Microbiol, vol. 37, pp. 1200-1202, 1999.
Loffler, J., et al.; "Comparison of different methods for extraction of DNA of fungal pathogens from cultures and blood," J Clin Microbiol, vol. 35, pp. 3311-3312, 1997.
McNeil, M., et al.; "Trends in Mortality Due to Invasive Mycotic Diseases in the United States, 1980-1997.," Clinical Infectious Diseases, vol. 33, pp. 641-647, 2001.
Munoz, P., et al.; "Update on invasive pulmonary aspergillosis: clinical and diagnostic aspects," Clin Microbiol Infect, vol. 12 Suppl 7, pp. 24-39, 2006.

(Continued)

*Primary Examiner* — Christopher M. Babic
(74) *Attorney, Agent, or Firm* — Merchant & Gould

(57) ABSTRACT

Provided are quantitative PCR-based compositions and methods for the diagnosis of invasive pulmonary aspergillosis (IPA) in a patient sample, such as bronchoalveolar lavage (BAL) fluid. The methods presented herein involve isolating a patient sample, optionally extracting DNA from the sample, carrying out a quantitative PCR (qPCR) reaction on the sample to generate an amplicon that includes a region of an *Aspergillus* spp. ribosomal RNA (rRNA) gene, and detecting the PCR amplicon. The present disclosure also provides primers and primer sets for specifically detecting an *Aspergillus* spp. fungal pathogen in the presence of human ribosomal DNA (rDNA).

14 Claims, 5 Drawing Sheets

PUBLICATIONS

Ou, C., et al.; "Use of UV irradiation to reduce false positivity in polymerase chain reaction," Biotechniques, vol. 10, pp. 442, 444, 446, 1991.

Paterson, R.; "Internal amplification controls have not been employed in fungal PCR hence potential false negative results," J Appl Microbiol, vol. 102, pp. 1-10, 2007.

Pfeiffer, C., et al.; "Diagnosis of invasive aspergillosis using a galactomannan assay: a meta-analysis," Clin Infect Dis, vol. 42, pp. 1417-1427, 2006.

Raad, I., et al.; "Diagnosis of invasive pulmonary aspergillosis using polymerase chain reaction-based detection of *Aspergillus* in BAL," Chest, vol. 121, pp. 1171-1176, 2002.

Rantakokko-Jalava, K., et al.; "Semiquantitative detection by real-time PCR of *Aspergillus fumigatus* in bronchoalveolar lavage fluids and tissue biopsy specimens from patients with invasive aspergillosis," J Clin Microbiol, vol. 41, pp. 4304-4311, 2003.

Reichenberger, F., et al. "Diagnostic yield of bronchoscopy in histologically proven invasive pulmonary aspergillosis," Bone Marrow Transplant, vol. 24, pp. 1195-1199, 1999.

Reichenberger, F., et al.; "Diagnosis and treatment of invasive pulmonary aspergillosis in neutropenic patients," Eur Respir J, vol. 19, pp. 743-755, 2002.

Saito, H., et al.; "Bronchoalveolar lavage in the diagnosis of pulmonary infiltrates in patients with acute leukemia," Chest, vol. 94, pp. 745-749, 1988.

Sanguinetti, M., et al.; "Comparison of real-time PCR, conventional PCR, and galactomannan antigen detection by enzyme-linked immunosorbent assay using bronchoalveolar lavage fluid samples from hematology patients for diagnosis of invasive pulmonary aspergillosis," J Clin Microbiol, vol. 41, pp. 3922-3925, 2003.

Segal, B., et al.; "Current approaches to diagnosis and treatment of invasive aspergillosis," Am J Respir Crit Care Med, vol. 173, pp. 707-717, 2006.

Spiess, B., et al.; "Development of a LightCycler PCR assay for detection and quantification of *Aspergillus fumigatus* DNA in clinical samples from neutropenic patients," J Clin Microbiol, vol. 41, pp. 1811-1818, 2003.

Spreadbury, C., et al.; "Detection of *Aspergillus fumigatus* by polymerase chain reaction," J Clin Microbiol, vol. 31, pp. 615-621, 1993.

Tuon, F.; "A systematic literature review on the diagnosis of invasive aspergillosis using polymerase chain reaction (PCR) from bronchoalveolar lavage clinical samples," Rev Iberoam Micol, vol. 24, pp. 89-94, 2007.

* cited by examiner

FIG. 3A

| | 1390 | 1400 | 1410 | 1420 | 1430 | |
|---|---|---|---|---|---|---|
| A. clavatus | CGAAAACGAA | CGAGACCTCG | GCCCT-TAAA | TAG---CCCG | GTCCGCATT | SEQ ID NO: 12 |
| A. fischerianus | CGATAACGAA | CGAGACCTCG | GCCCT-TAAA | TAG---CCCG | GTCCGCATT | SEQ ID NO: 13 |
| A. flavus | CGATAACGAA | CGAGACCTCG | GCCCT-TAAA | TAG---CCCG | GTCCGCGTT | SEQ ID NO: 14 |
| A. fumigatus | CGATAACGAA | CGAGACCTCG | GCCCT-TAAA | TAG---CCCG | GTCCGCATT | SEQ ID NO: 15 |
| A. nidulans | CGATAACGAA | CGAGACCTCG | GCCCT-TAAA | TAG---CCCG | GTCCGCGTC | SEQ ID NO: 16 |
| A. oryzae | CGATAACGAA | CGAGACCTCG | GCCCT-TAAA | TAG---CCCG | GTCCGCGTT | SEQ ID NO: 17 |
| A. terreus | CGATAACGAA | CGAGACCTCG | GCCCT-TAAA | TAG---CCCG | GTCCGCATT | SEQ ID NO: 18 |
| A. ustus | CGATAACGAA | CGAGACCTCG | GCCCT-TAAA | TAG---CCCG | GTCCGCGTC | SEQ ID NO: 19 |
| P. variotii | CGATAACGAA | CGAGACCTCG | GCCCT-TAAA | TAG---CCCG | GTCCGCGTT | SEQ ID NO: 20 |
| P. chrysogenum | CGATAACGAA | CGAGACCTCG | GCCCT-TAAA | TAG---CCCG | GTCCGCATT | SEQ ID NO: 21 |
| Asp18s F primer | -GATAACGAA | CGAGACCTCG | G--------- | ---------- | ---------- | SEQ ID NO: 1 |
| Asp18s probe | ---------- | ---------- | ---CT-TAAA | TAG---CCCG | GTCCGC--- | SEQ ID NO: 5 |
| Asp 18s R primer | ---------- | ---------- | ---------- | ---------- | ---------- | |
| C. albicans | CGATAACGAA | CGAGACCTTA | ACCTACTAAA | TAG---TGCT | GCTAGCATT | SEQ ID NO: 22 |
| S. cerevisiae | CGATAACGAA | CGAGACCTTA | ACCTACTAAA | TAG---TGGT | GCTAGCATT | SEQ ID NO: 23 |
| Human | CGATAACGAA | CGAGACTCTG | GCATGCTAAC | TAGTTACGCG | ACCCCCGAG | SEQ ID NO: 24 |

FIG. 3B

| | 1500 | 1510 | |
|---|---|---|---|
| A. clavatus | TGCGCGGGCAA | TAACAGGTCT GTC | SEQ ID NO: 25 |
| A. fischerianus | TGCGCGGGCAA | TAACAGGTCT GTC | SEQ ID NO: 26 |
| A. flavus | TGCGCGGGCAA | TAACAGGTCT GTC | SEQ ID NO: 27 |
| A. fumigatus | TGCGCGGGCAA | TAACAGGTCT GTC | SEQ ID NO: 28 |
| A. nidulans | TGCGCGGGCAA | TAACAGGTCT GTC | SEQ ID NO: 29 |
| A. oryzae | TGCGCGGGCAA | TAACAGGTCT GTC | SEQ ID NO: 30 |
| A. terreus | TGCGCGGGCAA | TAACAGGTCT GTC | SEQ ID NO: 31 |
| A. ustus | TGCGCGGGCAA | TAACAGGTCT GTC | SEQ ID NO: 32 |
| P. variotii | TGCGCGGGCAA | TAACAGGTCT GTC | SEQ ID NO: 33 |
| P. chrysogenum | TGCGCGGGCAA | TAACAGGTCT GTC | SEQ ID NO: 34 |
| Asp18s F primer | ------------ | ------------ | |
| Asp18s probe | ------------ | ------------ | |
| Asp 18s R primer | -GCGCGGGCAA | TAACAGGTCT --- | SEQ ID NO: 2 |
| C. albicans | TTTGAGGCAA | TAACAGGTCT GTC | SEQ ID NO: 35 |
| S. cerevisiae | TTTGAGGCAA | TAACAGGTCT GTC | SEQ ID NO: 36 |
| Human | ATTGAG-CAA | TAACAGGTCT GTC | SEQ ID NO: 37 |

FIGURE 4

*Aspergillus fumigatus* 18S rRNA Gene Sequence
(SEQ ID NO: 6)

AACCTGGTTGATCCTGCCAGTAGTCATATGCTTGTCTCAAAGATTAAGCCATGCA
TGTCTAAGTATAAGCAATTTATACGGTGAAACTGCGAATGGCTCATTAAATCAGT
TATCGTTTATTTGATAGTACCTTACTACATGGATACCTGTGGTAATTCTAGAGCTA
ATACATGCTAAAAACCTCGACTTCGGAAGGGGTGTATTTATTAGATAAAAAACC
AATGCCCTTCGGGGCTCCTTGGTGAATCATAATAACTTAACGAATCGCATGGCCT
TGCGCCGGCGATGGTTCATTCAAATTTCTGCCCTATCAACTTTCGATGGTAGGAT
AGTGGCCTACCATGGTGGCAACGGGTAACGGGGAATTAGGGTTCGATTCCGGAG
AGGGAGCCTGAGAAACGGCTACCACATCCAAGGAAGGCAGCAGGCGCGCAAAT
TACCCAATCCCGACACGGGGAGGTAGTGACAATAAATACTGATACGGGGCTCTT
TTGGGTCTCGTAATTGGAATGAGTACAATCTAAATCCCTTAACGAGGAACAATTG
GAGGGCAAGTCTGGTGCCAGCAGCCGCGGTAATTCCAGCTCCAATAGCGTATAT
TAAAGTTGTTGCAGTTAAAAAGCTCGTAGTTGAACCTTGGGTCTGGCTGGCCGGT
CCGCCTCACCGCGAGTACTGGTCCGGCTGGACCTTTCCTTCTGGGGAACCTCATG
GCCTTCACTGGCTGTGGGGGGAACCAGGACTTTTACTGTGAAAAAATTAGAGTGT
TCAAAGCAGGCCTTTGCTCGAATACATTAGCATGGAATAATAGAATAGGACGTG
CGGTTCTATTTTGTTGGTTTCTAGGACCGCCGTAATGATTAATAGGGATAGTCGG
GGGCGTCAGTATTCAGCTGTCAGAGGTGAAATTCTTGGATTTGCTGAAGACTAAC
TACTGCGAAAGCATTCGCCAAGGATGTTTTCATTAATCAGGGAACGAAAGTTAG
GGGATCGAAGACGATCAGATACCGTCGTAGTCTTAACCATAAACTATGCCGACT
AGGGATCGGGCGGTGTTTCTATGATGACCCGCTCGGCACCTTACGAGAAATCAA
AGTTTTTGGGTTCTGGGGGGAGTATGGTCGCAAGGCTGAAACTTAAAGAAATTG
ACGGAAGGGCACCACAAGGCGTGGAGCCTGCGGCTTAATTTGACTCAACACGGG
GAAACTCACCAGGTCCAGACAAAATAAGGATTGACAGATTGAGAGCTCTTTCTT
GATCTTTTGGATGGTGGTGCATGGCCGTTCTTAGTTGGTGGAGTGATTTGTCTGCT
TAATTGCGATAACGAACGAGACCTCGGCCCTTAAATAGCCCGGTCCGCATTT
GCGGGCCGCTGGCTTCTTAGGGGACTATCGGCTCAAGCCGATGGAAGTGCGCG
GCAATAACAGGTCTGTGATGCCCTTAGATGTTCTGGGCCGCACGCGCGCTACAC
TGACAGGGCCAGCGAGTACATCACCTTGGCCGAGAGGTCTGGGTAATCTTGTTA
AACCCTGTCGTGCTGGGGATAGAGCATTGCAATTATTGCTCTTCAACGAGGAATG
CCTAGTAGGCACGAGTCATCAGCTCGTGCCGATTACGTCCTGCCCTTTGTACAC
ACCGCCCGTCGCTACTACCGATTGAATGGCTCGGTGAGGCCTTCGGACTGGCTCA
GGGGAGTTGGCAACGACTCCCCAGAGCCGGAAAGTTGGTCAAACCCGGTCATTT
AGAGGAAGTAAAAGTCGTAACAAGGTTTCCGTAGGTGAACCTGCAGAAGGATCA
AG

US 8,450,059 B2

QUANTITATIVE PCR-BASED COMPOSITIONS AND METHODS FOR THE DIAGNOSIS OF INVASIVE PULMONARY ASPERGILLOSIS

CROSS REFERENCE TO RELATED APPLICATIONS

This application claims the benefit of U.S. Provisional Patent Application No. 61/173,065, filed Apr. 27, 2009, and which provisional patent application is incorporated by reference in its entirety herein.

GOVERNMENT SPONSORED RESEARCH

This disclosure was made, in part, in the course of research sponsored by the National Institutes of Health, Grant RO1 AI054703 from the National Institute of Allergy and Infectious Diseases. The U.S. government has certain rights in this disclosure.

SEQUENCE LISTING

The present application includes a Sequence Listing in electronic format as a txt file titled "Sequence_Listing_27Apr10," which was created on Apr. 27, 2010 and which has a size of 4 kilobytes (KB). The contents of txt file "Sequence_Listing_27Apr10" are incorporated by reference herein.

BACKGROUND OF THE DISCLOSURE

1. Technical Field of the Disclosure

The present disclosure is directed, generally, to the detection of fungal pathogens in a patient sample. More specifically, provided herein are quantitative PCR-based compositions and methods for the diagnosis of invasive pulmonary aspergillosis (IPA) in a patient sample, such as bronchoalveolar lavage (SAL) fluid. The methods presented herein involve isolating a sample, collecting a cell fraction from the sample, extracting DNA from the cell fraction, carrying out a quantitative PCR (qPCR) reaction on the sample to generate an amplicon that includes a region of an *Aspergillus* spp. gene (such as a ribosomal RNA (rRNA) gene), and detecting the PCR amplicon. The present disclosure also provides primers, primer sets, and kits for specifically detecting an *Aspergillus* spp. fungal pathogen in the presence of human DNA, including ribosomal DNA (rDNA).

2. Description of the Related Art

Invasive pulmonary aspergillosis (IPA) is a common infection in patients with hematological malignancies and those undergoing hematopoietic cell transplantation [1]. Despite the availability of new mould-active antifungal medications such as extended spectrum azoles (e.g., voriconazole and posaconazole) and echinocandins, aspergillosis remains a significant cause of death in patients with cancer [2]. Delays in the institution of appropriate antifungal therapy may contribute to the high mortality seen with IPA, and the diagnosis of aspergillosis remains a clinical challenge, enhancing the potential for delay [1, 3, 4].

Most symptoms of IPA are non-specific, such as fever, cough, or chest pain, and many patients have no symptoms at all. Although some radiographic findings in the lungs can suggest aspergillosis, such as the presence of a halo sign (ground glass opacity surrounding a nodule) or cavitating nodules, these findings can also be found in subjects with pulmonary zygomycosis or other infections and, thus, are not necessarily specific [5]. The failure to make an accurate diagnosis frequently results in the use of empirical antifungal therapy in the suitable immunocompromised host.

The diagnosis of IPA remains challenging. Bronchoalveolar lavage (BAL) fluid is routinely used to assess the presence of fungi at the site of pulmonary infection. Conventional microbiological techniques like culture and histology of BAL fluid are most commonly used for the diagnosis of IPA, but have suboptimal sensitivity and, in the case of culture, may take several days [6-8]. Detection of the fungal cell wall constituents like galactomannan (in serum and BAL fluid) and beta-glucan (in serum) are promising diagnostic alternatives to facilitate the diagnosis of invasive fungal infection, but false positive and false negative results remain problematic with both assays [9-11].

Molecular diagnostic techniques such as nucleic acid detection by PCR are emerging as potentially more sensitive and rapid alternatives to conventional techniques for the diagnosis of IPA [12-19], but published studies lack key quality control standards that are useful in identifying problems with false negative and false positive results within a study. Furthermore, the lack of appropriate controls affects the ability to coherently compare different published diagnostic PCR platforms for IPA [12, 21, 22, 25].

Quantitative PCR has several advantages when used for the detection of *Aspergillus* spp. First, qPCR is highly sensitive with the potential to detect a few gene copies per reaction, or less than a single genome for multicopy genes such as the rRNA gene. Second, by taking advantage of both conserved and variable regions of genes, primers and probes can be made that are specific for a given genus, species or strain of microbe. Third, qPCR can measure the amount of microbial DNA in a clinical sample, which may be useful for assessing the burden of infection and in distinguishing between colonization and infection. Fourth, multiplexed qPCR reactions can reduce the necessity of running independent qPCRs allowing for the detection of multiple targets or for inclusion of amplification controls in a single reaction. Fifth, qPCR assays can be completed in a few hours, resulting in a rapid turn around time for reporting results.

To develop an optimal qPCR assay for diagnosis, however, several challenges and shortcomings must be addressed to minimize false positive and false negative results [20-22]. False negatives can occur due to suboptimal DNA extraction (i.e. low recovery of DNA and/or the presence of PCR inhibitors), large quantities of human genomic DNA competing with the microbial target for amplification, and suboptimal analytical sensitivity of the qPCR reaction itself (high detection threshold). False positives can occur due to introduction of contamination during sample collection, DNA extraction, and PCR set-up, resulting from the presence of fungi in the environment or fungal PCR product carry-over. In addition, false positives can occur in the setting of suboptimal analytical specificity in the qPCR, resulting from cross-reactivity of the target qPCR assay with other (non-target) fungi or DNA. Accordingly, optimal qPCR assays for IPA should incorporate controls to assess for the factors contributing to false positive and false negative results.

What is critically needed in the art are compositions and methods for achieving the diagnosis of invasive pulmonary aspergillosis. Ideally, such compositions and methods would employ quality control measures to address false positives and negatives which can hinder accurate evaluation of diagnostic performance.

SUMMARY OF THE INVENTION

The present disclosure addresses these and other related needs by providing, inter alia, quantitative PCR (qPCR) compositions and methods for the detection of *Aspergillus* DNA in a patient sample. The compositions and methods described herein offer the potential for earlier diagnosis and higher sensitivity detection of *Aspergillus* DNA and further provide quality control measures that overcome the problem of false positives and negatives. Thus, the present disclosure provides an optimized qPCR assay platform for the diagnosis of IPA, which, optionally, further comprises one or more of a panel of qPCR assays, including amplification and extraction controls and a modified DNA extraction technique to increase yields of fungal DNA from BAL fluid.

Thus, within certain embodiments, the present disclosure provides primer sets for the diagnosis of invasive pulmonary aspergillosis (IPA), wherein the primer sets comprise a forward primer and a reverse primer that are capable of amplifying a region of one or more *Aspergillus* spp gene(s), such as a ribosomal RNA (rRNA) gene, for example an 18S rRNA gene. Exemplified herein are primer sets wherein the forward primer comprises the nucleotide sequence 5'-GAT AAC GAA CGA GAC CTC GG-3' (SEQ ID NO: 1) and the reverse primer comprises the nucleotide sequence 5'-AGA CCT GTT ATT GCC GCG C-3' (SEQ ID NO: 2). The primer sets disclosed herein may be used in methods for the detection of one or more *Aspergillus* spp selected from the group consisting of *Aspergillus fumigatus, Aspergillus oryzae, Aspergillus ustus, Aspergillus candidus, Aspergillus terreus,* and *Aspergillus flavus*.

Within other embodiments, the present disclosure provides kits for the diagnosis of invasive pulmonary aspergillosis (IPA), wherein the kits comprise (1) a primer set comprising a forward primer and a reverse primer wherein said forward primer and said reverse primer are capable of generating a PCR amplicon from a region of one or more *Aspergillus* spp gene(s) and (2) a probe capable of hybridizing to said PCR amplicon. Within certain aspects, the kits according to these embodiments may further comprise an internal amplification control (IAC) primer set comprising a second forward primer and a second reverse primer wherein the second forward primer and the second reverse primer are capable of generating a PCR amplicon from a region of a second gene having a nucleotide sequence that is unrelated to said *Aspergillus* spp gene. Exemplified herein is and IAC primer set wherein the second forward primer comprises the nucleotide sequence 5'-GCC TGG TGC AAA AAT TGC TTA TC-3' (SEQ ID NO: 3) and wherein said second reverse primer comprises the nucleotide sequence 5'-CTA AGA CAA GTG TGT TTA TGG TAT TG-3' (SEQ ID NO: 4) targeting the jellyfish aequorin gene.

Still further embodiments of the present disclosure provide quantitative PCR methods for the diagnosis of invasive pulmonary aspergillosis (IPA) in a patient sample. These methods comprise the steps of: (a) isolating a sample, such as bronchoalveolar lavage (BAL) fluid, from the patient, (b) collecting a cell fraction from the sample, (c) extracting DNA from the cell fraction, (d) carrying out a quantitative PCR (qPCR) reaction on the patient sample with a primer set that permits the generation of an amplicon that includes a region of an *Aspergillus* spp. gene, and (e) detecting the PCR amplicon; wherein the presence of the PCR amplicon indicates a positive diagnosis of IPA.

Within certain aspects of these methods, the *Aspergillus* spp. gene is a ribosomal RNA (rRNA) gene such as an 18S rRNA gene. As described above and exemplified herein, a suitable primer set for the amplification of an *Aspergillus* spp. 18S rRNA gene comprises a forward primer comprising the nucleotide sequence 5'-GAT AAC GAA CGA GAC CTC GG-3' (SEQ ID NO: 1) and a reverse primer 5'-AGA CCT GTT ATT GCC GCG C-3' (SEQ ID NO: 2). Optionally, the PCR amplicon may be detected by hybridizing a probe comprising the nucleotide sequence 5'-FAM CTT AAA TAG CCC GGT CCG C BHQ-3' (SEQ ID NO: 5).

These and other aspects of the present disclosure will become apparent upon reference to the following detailed description and attached drawings. All publications, patents, and patent applications cited herein, whether supra or infra, are hereby incorporated by reference in their entirety.

BRIEF DESCRIPTION OF THE FIGURES

FIG. 3A is a primer/probe map for a range of *Aspergillus* 18s rRNA.

FIG. 3B is a primer/probe map for a range of *Aspergillus* 18s rRNA.

FIG. 4 is the nucleotide sequence for *Aspergillus fumigatus* 18s rRNA gene (SEQ ID NO: 6) indicating the positions of forward and reverse primers (SEQ ID NOs: 1 and 2) and probe (SEQ ID NO: 3).

DETAILED DESCRIPTION OF THE DISCLOSURE

Figure 1:
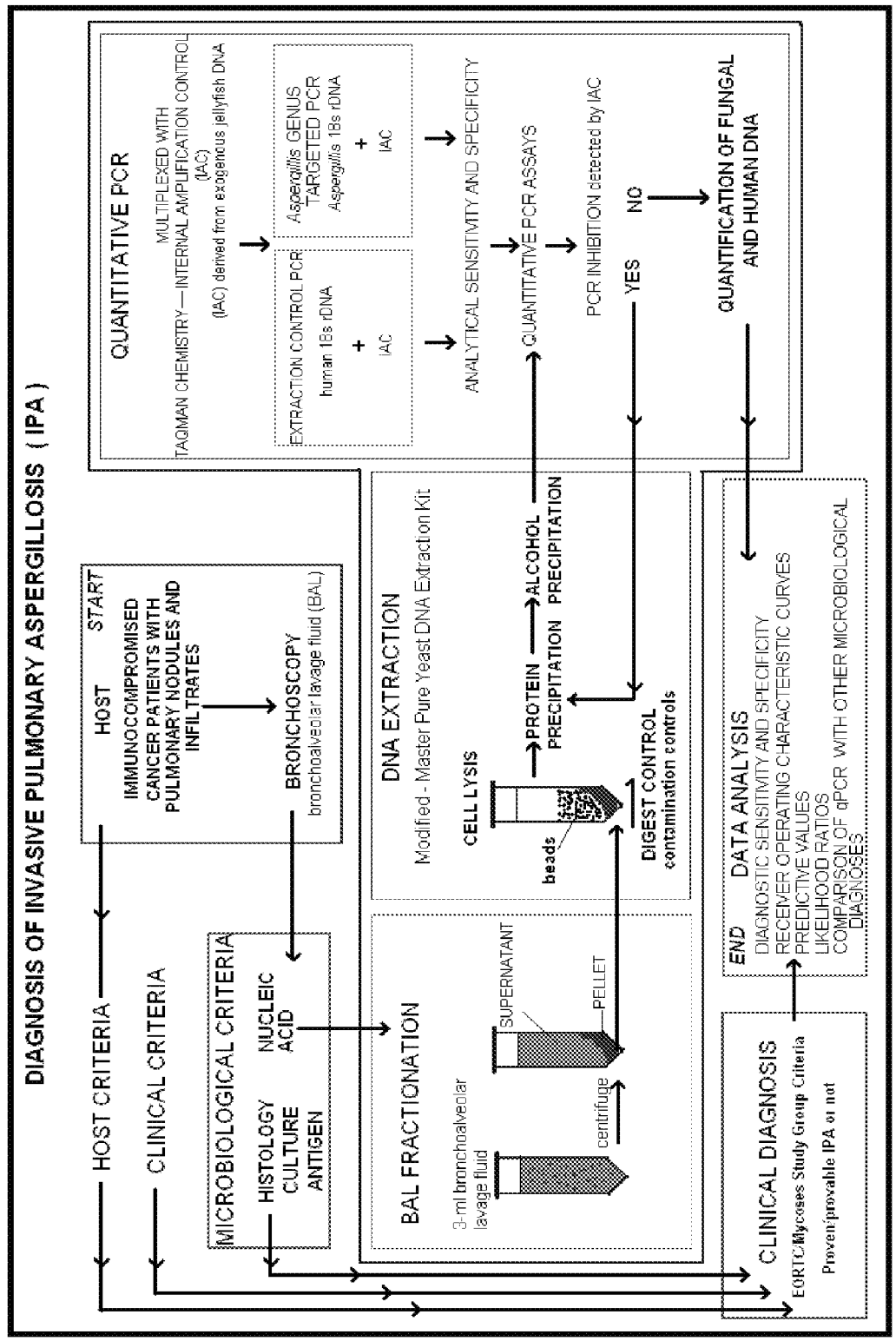
FIG. 1 is a flowchart depicting an algorithm used in the methods described herein for the diagnosis of IPA using qPCR.

As indicated above, the present disclosure is based upon the development of an *Aspergillus* qPCR assay that is capable of detecting *Aspergillus* DNA in concentrated BAL fluid pellet fractions from subjects with proven or probable invasive pulmonary aspergillosis (IPA). As described herein, the presently disclosed qPCR approach for the diagnosis of IPA may, optionally, incorporate one or more quality control step(s) that is/are designed to determine (1) if fungal contamination is introduced at the DNA extraction or PCR set up stages, (2) if human DNA is present in the extracted samples and at what level (extraction control), (3) if PCR inhibitors are present after DNA extraction and to what extent they cause inhibition (internal amplification control), and/or (4) if large amounts of human genomic DNA impede the *Aspergillus* qPCR.

The present disclosure will be best understood by reference to the following definitions:

DEFINITIONS

An "individual" or "subject", "mammal", "patient" or "animal", as used herein, refers to vertebrates that support a fungal infection, including, but not limited to, birds (such as water fowl and chickens) and members of the mammalian species, such as canine, feline, lupine, mustela, rodent (racine, and murine, etc.), equine, bovine, ovine, caprine, porcine species, and primates, the latter including humans.

As used herein, the term "isolated" means that the referenced material is removed from its native environment, e.g., a cell or fungus. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e. contaminants, including native materials from which the material is obtained. For example, a purified fungal DNA is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Techniques to isolate and purify specific nucleic acids and proteins are well known to those of skill in the art. In accordance with the present disclosure there may be employed conventional molecular biology, microbiology, and recombinant DNA techniques within the skill of the art. Such techniques are explained fully in the literature. See, e.g., Sambrook et al., Molecular Cloning: A Laboratory Manual, Second Edition (Cold Spring Harbor, N.Y.: Cold Spring Harbor Laboratory Press, 1989) ("Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); Perbal, "A Practical Guide To Molecular Cloning" (Ausubel, F. M. et al. eds., (1984)). Current Protocols in Molecular Biology (John Wiley & Sons, Inc., 1994). These techniques include site directed mutagenesis employing oligonucleotides with altered nucleotides for generating PCR products with mutations (e.g., the "Quikchange" kit manufactured by Stratagene).

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated.

In a specific embodiment, the term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

The term "sample" as used in the present disclosure can be any tissue, fluid, or other source of DNA from a patient or mammal.

The terms "nucleic acid" and "oligonucleotide," as used herein, refer to polydeoxyribonucleotides (containing 2-deoxy-D-ribose), to polyribonucleotides (containing D-ribose), and to any other type of polynucleotide which is an N glycoside of a purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA. For use in the present disclosure, an oligonucleotide also can comprise non-purine or non-pyrimidine nucleotide analogs. The length of a nucleic acid sequence is referred to as the number of "base pairs (bp)" present in the double-stranded nucleic acid sequence.

The nucleic acid molecules of sequences disclosed herein are written according to The International Union of Pure and Applied Chemistry (IUPAC) DNA codes. Specifically, "A" is Adenine, "C" is Cytosine, "G" is Guanine, "T" is Thymine, "U" is Uracil, "R" is any Purine (A or G), "Y" is any Pyrimidine (C, T, or U), "M" is C or A, "K" is T, U, or G, "W" is T, U, or A, "S" is C or G, "B" is C, T, U, or G (not A), "D" is A, T, U, or G (not C), "H" is A, T, U, or C (not G), "V" is A, C, or G (not T, not U), and "N" is any base (A, C, G, T, or U).

In certain embodiments, the amount of fungal DNA present in a sample is described in terms of the "fold-excess" of human or non-fungal DNA over the amount of fungal DNA present in the same sample. For example, if 1 µg of human genomic DNA is present in a sample that has 0.001 µg of fungal DNA, then the human DNA is understood to be in 1000-fold excess of the fungal DNA.

Oligonucleotides can be prepared by any suitable method, including direct chemical synthesis by a method such as the phosphotriester method of Narang et al. (1979) *Meth. Enzymol.* 68:90-99; the phosphodiester method of Brown et al., (1979) *Meth. Enzymol.* 68:109-151; the diethylphosphoramidite method of Beaucage et al. (1981) *Tetrahedron Lett.* 22:1859-1862; and the solid support method of U.S. Pat. No. 4,458,066, each incorporated herein by reference. A review of synthesis methods of conjugates of oligonucleotides and modified nucleotides is provided in Goodchild (1990) *Bioconjugate Chemistry* 1(3):165-187, incorporated herein by reference.

The term "primer," as used herein, refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein. As used herein, a "forward primer" is understood to mean a primer that is capable of hybridizing to a region of DNA along the 5' (coding) strand of DNA. A "reverse" primer is understood to mean a primer that is capable of hybridizing to a region of DNA along the 3' (non-coding) strand of DNA.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

A "primer set" or "primer pair" refers to a specific combination of a forward primer and a reverse primer. The "primer set" or "primer pair" may be used in a PCR reaction to generate a specific PCR product or amplicon.

The term "amplicon" as used herein, refers to the DNA sequence generated by a PCR or qPCR reaction. "Amplicon" may further be used synonymously with the term "PCR product."

In certain embodiments, the term "primer" is also intended to encompass the oligonucleotides used in ligation-mediated amplification processes, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

The terms "target, "target sequence", "target region", and "target nucleic acid," as used herein, are synonymous and refer to a region or subsequence of a nucleic acid which is to be amplified or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., (1989) Molecular Cloning—A Laboratory Manual (Cold Spring Harbor Laboratory, Cold Spring Harbor, N.Y.); and Wetmur (1991) *Critical Review in Biochem. and Mol. Biol.* 26(3/4):227-259; both incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription and the polymerase chain reaction (PCR), including Real Time PCR (see U.S. Pat. Nos. 4,683,195 and 4,683,202; PCR Protocols: A Guide to Methods and Applications (Innis et al., eds, 1990)). Exemplary "amplification reactions conditions" or "amplification conditions" typically comprise either two or three step cycles. Two step cycles have a denaturation step followed by a hybridization/elongation step. Three step cycles comprise a denaturation step followed by a hybridization step followed by a separate elongation step.

Polymerase chain reaction (PCR) is a method that allows exponential amplification of short DNA sequences (usually 100 to 600 bases) within a longer double stranded DNA molecule. PCR entails the use of a pair of primers, each about 20 nucleotides in length, that are complementary to a defined sequence on each of the two strands of the DNA. These primers are extended by a DNA polymerase so that a copy is made of the designated sequence. After making this copy, the same primers can be used again, not only to make another copy of the input DNA strand but also of the short copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is analyzed on an agarose gel and is abundant enough to be detected with an ethidium bromide stain.

In other embodiments, real-time PCR, also called quantitative real time PCR, quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample. For example, in the embodiments disclosed herein, qPCR may be used to quantify the amount of fungal DNA in a patient sample. The procedure follows the general principle of PCR; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce upon binding to complementary DNA (such as with molecular beacons) or with completion of each PCR cycle (such as with dual labeled probes rendered more fluorescent with the 5' exonuclease activity of polymerase enzymes).

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., (1991) *Gene* 108:1), *E. coli* DNA polymerase I (Lecomte and Doubleday (1983) *Nucleic Acids Res.* 11:7505), T7 DNA polymerase (Nordstrom et al. (1981) *J. Biol. Chem.* 256: 3112), *Thermus thermophilus* (Tth) DNA polymerase (Myers and Gelfand (1991) *Biochemistry* 30:7661), *Bacillus stearothermophilus* DNA polymerase (Stenesh and McGowan (1977) *Biochim Biophys Acta* 475:32), *Thermococcus litoralis* (Tli) DNA polymerase (also referred to as Vent DNA polymerase, Cariello et al. (1991) *Nucleic Acids Res* 19:4193), *Thermotoga maritima* (Tma) DNA polymerase (Diaz and Sabino (1998) *Braz J. Med. Res* 31:1239), *Thermus aquaticus* (Taq) DNA polymerase (Chien et al., (1976) *J. Bacteoriol* 127:1550), *Pyrococcus kodakaraensis* KOD DNA polymerase (Takagi et al. (1997) *Appl. Environ. Microbiol.* 63:4504), JDF-3 DNA polymerase (Patent application WO 0132887), and *Pyrococcus* GB-D (PGB-D) DNA polymerase (Juncosa-Ginesta et al. (1994) *Biotechniques* 16:820). The polymerase activity of any of the above enzymes can be determined by means well known in the art.

As used herein, a primer is "specific," for a target sequence if, when used in an amplification reaction under sufficiently stringent conditions, the primer hybridizes primarily only to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

It is understood in the art that a nucleic acid molecule need not be 100% complementary to a target nucleic acid sequence to be specifically hybridizable. That is, two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "non-specific amplification," as used herein, refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and is apt to occur especially during the lower temperature, reduced stringency, pre-amplification conditions.

The term "primer dimer," as used herein, refers to a template-independent non-specific amplification product, which is believed to result from primer extensions wherein another primer serves as a template. Although primer dimers frequently appear to be a concatamer of two primers, i.e., a dimer, concatamers of more than two primers also occur. The term "primer dimer" is used herein generically to encompass a template-independent non-specific amplification product.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the disclosure.

For the purposes of this disclosure, the term "activated," as used herein, refers to a primer or other oligonucleotide that is capable of participating in a reaction with DNA polymerase or DNA ligase. A primer or other oligonucleotide becomes activated when it hybridizes to a substantially complementary nucleic acid sequence and is chemically modified so that it can interact with a DNA polymerase or a DNA ligase. For example, when the oligonucleotide is a primer, and the primer is hybridized to a template, a 3'-blocking group can be removed from the primer by, for example, a cleaving enzyme such that DNA polymerase can bind to the 3' end of the primer and promote primer extension.

The term "fluorescent generation probe" refers either to a) an oligonucleotide having an attached fluorophore and quencher, and optionally a minor groove binder or to b) a DNA binding reagent such as Sybr® green dye.

The terms "fluorescent label" or "fluorophore" refers to compounds with a fluorescent emission maximum between about 350 and 900 nm. A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein ([4,7,2',4',5'-hexachloro-(3',6'-dipivaloylfluoresceinyl)-5-carboxylic acid]); 5-Tetra-chloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), Quasar-670 (Biosearch Technologies), CalOrange (Biosearch Technologies), Rox, as well as suitable derivatives thereof.

The term "ligation" as used herein refers to the covalent joining of two polynucleotide ends. In various embodiments, ligation involves the covalent joining of a 3' end of a first polynucleotide (the acceptor) to a 5' end of a second polynucleotide (the donor). Ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

As used herein, "ligase" refers to an enzyme that is capable of covalently linking the 3' hydroxyl group of a nucleotide to the 5' phosphate group of a second nucleotide. Examples of ligases include *E. coli* DNA ligase, T4 DNA ligase, etc.

The ligation reaction can be employed in DNA amplification methods such as the "ligase chain reaction" (LCR), also referred to as the "ligase amplification reaction" (LAR), see Barany (1991) *Proc. Natl. Acad. Sci. U.S.A.* 88:189; and Wu and Wallace (1989) *Genomics* 4:560, incorporated herein by reference. In LCR, four oligonucleotides, two adjacent oligonucleotides which uniquely hybridize to one strand of the target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes, see Segev PCT Pub. No. WO/9001069.

As used herein, the term "conserved region" or "conserved sequence" refers to a nucleic acid sequence in a region of a gene that is the same or highly similar across different species. For example, a sequence or region of a gene that is conserved may have the same nucleic acid sequence in several types of fungal species, or, in some cases, may have the same or highly similar sequence across different taxonomic phyla (e.g., a human DNA sequence and a fungal DNA sequence in a highly conserved region of a gene may be the same or highly similar). Conversely, a "highly variable" or "hypervariable" region or sequence of gene is not conserved across species or phyla, and will have many nucleotides differences in the hypervariable region in the gene from each species.

Methods for Diagnosing Invasive Pulmonary Aspergillosis (IPA)

As described above, *Aspergillus* fungal infections remain a major cause of morbidity and mortality in immunocompromised patients. Cultivation-based methods have poor diagnostic sensitivity for many fungal infections, which has led to the adoption of other diagnostic approaches such as detection of fungal antigens. There remains a need in the art for reliable methods for the detection of *Aspergillus* spp fungal pathogens, especially in the context of human DNA (in samples from infected patients, human and fungal DNA are mixed together).

Thus, disclosed herein are methods for detecting one or more *Aspergillus* spp fungal pathogen(s) in a patient sample. The methods disclosed herein target an *Aspergillus* spp gene, such as an *Aspergillus* spp rRNA gene. Exemplified herein are methods that target an *Aspergillus* spp 18S rRNA gene. The human rRNA operon is a continuous sequence made of the 18S, ITS1, 5.8S, ITS2, and 28S subunit regions, and has considerable sequence homology with the *Aspergillus* spp rRNA operon. Thus, a critical aspect of the present disclosure provides methods and PCR primers which do not cross-react with human DNA. The present disclosure provides PCR primers which amplify regions of an *Aspergillus* spp 18S rRNA gene specifically because they are discovered to have less cross-reactivity to human DNA. This is especially critical for the identification of *Aspergillus* spp DNA in patient samples, which also contain human DNA.

In certain aspects of the disclosure, the method includes the steps of (a) isolating a patient sample, (b) carrying out a PCR reaction on the patient sample to generate a PCR amplicon that includes a region of an *Aspergillus* spp gene, such as an *Aspergillus* spp ribosomal RNA (rRNA) gene, wherein the PCR reaction uses a primer set having a forward primer and a reverse primer wherein at least one of the forward primer and the reverse primer is complementary to the *Aspergillus* spp gene, and (c) detecting the PCR amplicon. The patient sample may be, for example, a bronchoalveolar lavage (BAL) fluid sample.

The PCR reaction carried out on the patient sample may be performed according to any of the methods known in the art. The purpose of the PCR reaction is to amplify a target sequence within an *Aspergillus* spp fungal DNA sequence, thereby generating a PCR amplicon. Preferably, the region amplified by the PCR reaction is in the 18S region of the *Aspergillus* spp rRNA gene. The PCR assays of the present disclosure target this region without cross-reacting with or being inhibited by the presence of human DNA.

In certain embodiments, quantitative PCR reactions are used to detect *Aspergillus* spp DNA in a sample. In other embodiments, qPCR reactions are used to detect *Aspergillus* spp DNA in a sample. In yet other embodiments, alternative methods other than PCR, such as ligase chain reaction, may be used to detect the presence of *Aspergillus* spp DNA in a sample. Alternatively, Nucleic Acid Sequence Based Amplification (NASBA) could be used to amplify *Aspergillus* spp rRNA directly from tissues using these primers. Any method suitable for amplifying a region of the target fungal gene (rDNA) or rRNA is contemplated in the present disclosure.

In certain aspects of the present disclosure, the methods for detecting an *Aspergillus* spp disclosed herein further involve the step of sequencing the PCR amplicon derived from sequencing. In some aspects, the PCR amplicon is between 50 and 1000 base pairs, and preferably, between 75 and 400 base pairs. Smaller amplicon sizes are desirable, since they are easier to sequence and useful for qPCR reactions. However, it is also important that the amplicon be large enough to facilitate accurate species identification, e.g., enhance resolution among different *Aspergillus* spp species.

Sequencing of the PCR amplicon may be carried out according to any methods known in the art suitable for determining the sequence of a PCR amplicon. The sequences of the PCR amplicons disclosed in the present invention are unique to each *Aspergillus* spp, thereby allowing identification of the specific species of *Aspergillus* DNA in a sample.

In certain embodiments, methods for the detection of *Aspergillus* spp DNA involving the step of carrying out a PCR reaction on a patient sample are provided, wherein each primer of the primer set in the PCR reaction specifically binds only to an *Aspergillus* spp DNA. Preferably, each primer of the primer set specifically binds only to an *Aspergillus* spp DNA in the presence of a non-*Aspergillus* DNA. In some embodiments, the non-fungal DNA is mammalian DNA. In other embodiments, the mammalian DNA is human DNA. In yet other embodiments, the non-Aspergillus DNA is in greater than 1,000,000-fold, 5,000,000-fold, or 30,000,000-fold mass excess of the *Aspergillus* DNA.

Primer Sequences for Identifying *Aspergillus* spp DNA

In certain embodiments of the present disclosure, specific sequences of the forward and reverse primers of the PCR reaction for identifying-DNA are disclosed. In certain embodiments, the forward and reverse primers of the PCR reaction are complementary to an *Aspergillus* spp 18S rRNA gene. In still other embodiments, the forward primer comprises the nucleotide sequence 5'-GAT AAC GAA CGA GAC CTC GG-3' (SEQ ID NO: 1) and the reverse primer comprises the nucleotide sequence 5'-AGA CCT GTT ATT GCC GCG C-3' (SEQ ID NO: 2).

In certain embodiments disclosed herein, a primer set for detecting an *Aspergillus* spp DNA by PCR is provided, wherein the primer set includes a forward primer and a reverse primer wherein at least one of the forward primer and the reverse primer is complementary to an *Aspergillus* spp gene, such as a ribosomal RNA (rRNA) gene. In certain embodiments, the forward primer or the reverse primer of the primer set is complementary to a sequence within an *Aspergillus* spp 18S rRNA gene.

It is to be understood in the present disclosure that any of the primer sequences disclosed herein may be modified without departing from the intended scope of the disclosure. Specifically, nucleotide substitutions, deletions and/or additions may be introduced into any of the primer sequences disclosed herein without altering the ability of the primers to identify *Aspergillus* spp DNA. Moreover, it is to be understood that the lengths of the primers may be shorter or longer than the sequences disclosed herein.

In certain embodiments of the present disclosure, methods and primer sets for detecting *Aspergillus* spp DNA are provided which detect DNA from an *Aspergillus* species such as, but not limited to *Aspergillus fumigatus*; *Aspergillus niger*; *Aspergillus oryzae*; and *Aspergillus terreus*.

The present disclosure also contemplates internal amplification control (IAC) primer sets that comprise a second forward primer and a second reverse primer wherein the second forward primer and the second reverse primer are capable of generating a PCR amplicon from a region of a second gene having a nucleotide sequence that is unrelated to the *Aspergillus* spp gene. Exemplified herein is and IAC primer set wherein the second forward primer comprises the nucleotide sequence 5'-GCC TGG TGC AAA AAT TGC TTA TC-3' (SEQ ID NO: 3) and wherein said second reverse primer comprises the nucleotide sequence 5'-CTA AGA CAA GTG TGT TTA TGG TAT TG-3' (SEQ ID NO: 4) for amplification of an exogenously added segment of the jellyfish aequorin gene DNA.

All U.S. patents, U.S. patent application publications, U.S. patent applications, foreign patents, foreign patent applications, non-patent publications, figures, tables, and websites referred to in this specification are expressly incorporated herein by reference, in their entirety.

EXAMPLES

Example 1

Methods and Procedures

This example describes methods and procedures employed in the present disclosure.

Study Population and Design

Patients with hematological malignancies or undergoing hematopoietic cell transplantation at the Seattle Cancer Care Alliance who developed pneumonia or pulmonary nodules underwent bronchoscopy with BAL. BAL fluid remaining after conventional microbiological and cytologic evaluations was processed as noted below. This was a retrospective study analyzing BAL fluid samples obtained from April 2002 to July 2003, and was approved by the Institutional Review Board at the Fred Hutchinson Cancer Research Center. This study involved 81 patients, 94 episodes of pneumonia, and 144 BAL samples. Note that multiple lobes were lavaged at the time of bronchoscopy in most subjects, resulting in an average of more than one BAL sample per episode. Analysis was done on an episode basis, with an episode defined as a single radiographically and temporally related pneumonia. If a subject had resolution of pulmonary infiltrates with appearance of a new infiltrate at a later time, this was considered a separate episode.

FIG. 1 depicts the algorithm used for the diagnosis of IPA using qPCR. Patients with proven or probable IPA were diagnosed using European Organization for Research and Treatment of Cancer/Mycoses Study Group (EORTC/MSG) criteria [23]. Designation of clinical status was performed by an investigator who was blinded to qPCR results, with host factors, clinical criteria, and microbiological criteria abstracted from the medical record and entered into a relational database.

Processing of BAL Fluid

The starting volume of BAL fluid was in the range of 2 to 5 ml. BAL fluid was centrifuged at 3200 rcf for 15 min at 4° C. The pellet was resuspended in a small volume of supernatant, with the final pellet fraction having a volume of 100 to 400 depending on the degree of cellularity. The pellet and the remaining supernatant fraction were frozen in separate tubes at −80° C. until DNA extraction.

DNA Extraction from BAL Fractions

BAL pellet and supernatant fractions were assayed separately in order to identify the most useful fraction for diagnosis. As disclosed herein, the majority of *Aspergillus* DNA in BAL fluid was cell-associated, most likely as either intact fungal cells or as fungi engulfed by leukocytes. Accordingly, it is contemplated that the BAL fluid pellet is the best fraction for use in the diagnosis of IPA and that diagnostic yield may increase by centrifuging large volumes of BAL fluid and subjecting the pellet to a single extraction.

*Aspergillus conidia* are ubiquitous in the environment, creating the potential for false positive fungal PCR results when highly sensitive PCR assays are employed [21]. Fungal cells or fungal DNA can enter the assay process at numerous points, including at the time of BAL collection, during DNA extraction, or at qPCR set up. Apart from processing samples in a laminar flow hood within a laboratory that was exclusively used for pre-PCR processing, UV irradiation, filtration of solutions, and baking of beads and glassware was further employed to eliminate potential contaminants present in the extraction and PCR reagents [26-28]. The Yeast Cell Lysis Solution™ and the Protein Precipitation Reagent™ (Epicentre® Biotechnologies, Madison, Wis.) used in DNA extraction may be UV irradiated without loss of function.

Silicon carbide sharps used in the bead beating step of DNA extraction were specifically chosen from a wide array of materials for their ability to remain chemically and physically stable through a 2-day baking period required to eliminate any contaminating nucleic acids. The organic solvents used in DNA extraction were filtered through a membrane with MWCO of 30 kDa. The qPCR mastermix reagents were carefully selected such that they could all be filtered through a membrane of 100 kDa MWCO.

The nucleotide cut-off for a 30 kDa filter was 60 bases of single stranded DNA and 50 bp double stranded DNA, and for a 100 kDa filter was 300 bases single stranded DNA and 125 bp double stranded DNA. Even though the *Aspergillus* qPCR amplicon described herein was 114 bp long (estimated MW of 70 kDa in its double stranded form), contamination of the PCR reagents was consistently prevented.

To minimize any contamination emerging from the IAC qPCR, the IAC primers, probe and template, which were multiplexed with the target qPCR assays, were also filtered as part of the mastermix. The size of the IAC template was designed to be 105 bases long such that it could easily filter through a membrane of 100 kDa MWCO.

Another source of contamination in PCR assays may arise from amplicon carry-over contamination from previous PCR runs of the same assay. In addition to strictly isolating pre- from post-PCR work, a uracil-N-glycosylase (UNG) enzyme step was incorporated prior to PCR in combination with use of the nucleotide 2'-deoxyuridine 5'-triphosphate (dUTP) to degrade previous PCR products and prevent carry-over contamination. Water-only sham digest controls and no-template PCR controls were used with every experiment and were consistently negative eliminating the possibility of contamination originating from the DNA extraction and PCR set ups.

DNA extraction of clinical samples and PCR set up was performed in a laminar flow hood within a laboratory that was exclusively used for pre-PCR processing. An optimized version of the MasterPure™ Yeast DNA Purification Kit (Epicentre® Biotechnologies, Madison, Wis.) was used for BAL DNA extraction. The 100% isopropanol, 70% ethanol and DNA grade water used for extraction were filtered in an Amicon Ultra-15 centrifugal filter unit with a molecular weight cut-off (MWCO) of 30 kDa (Millipore Corporation, Billerica, Mass.). Yeast Cell Lysis™ solution and MPC Protein Precipitation Reagent™ were UV irradiated at 240 mJ/cm$^2$ with samples approximately 15 centimeters from the bulbs (Spectrolinker™, Westbury, N.Y.). The silicon carbide sharps were washed 10 times in DNA free water and baked at 180° C. for 48 h. DNA-free microcentrifuge tubes were used with DNA extraction (Eppendorf Biopur tubes, Eppendorf AG, Hamburg, Germany). Sham digest controls including DNA free water were processed with every extraction run serving as negative controls to monitor for fungal contamination.

Preparation of Fungal Genomic DNA

Although qPCR assays can detect down to a few target molecules of template per reaction, DNA extraction of fungal pathogens from clinical samples remains the bottleneck of PCR diagnostics [29-31]. Each BAL sample may include sterile saline (lavage fluid), fungal cells, biological components which may be PCR inhibitors (e.g., heme and mucus), and a large amount of human cells.

The MasterPure™ Yeast DNA Purification Kit (Epicentre® Biotechnologies, Madison, Wis.) was selected based on optimizing fungal DNA yields and minimizing FP and FN results. The DNA extraction protocol was further optimized by adding silicon carbide sharps for lysis of fungal cell wall which significantly enhanced extraction yields. The extraction control qPCR qualitatively confirmed successful extractions and gave a quantitative measure of the amount of human genomic DNA present in every BAL extract. In addition, it helped guarantee that the BAL fluid contacted a human mucosal surface and that DNA was not significantly degraded.

The processing and extraction of fungal cells from external sources was avoided to minimize the potential for false positive PCR results. The ability of the presently disclosed *Aspergillus* qPCR assay to successfully amplify 10 fg of *A. fumigatus* genomic DNA (<1 *Aspergillus* genome) in the presence of 1 µg of human genomic DNA per reaction ($10^9$ fold excess human DNA) was tested. The human 18S rRNA gene PCR extraction control measurements helped validate that human genomic DNA in actual PCR reactions derived from BAL fluid was well within these limits, providing evidence that human DNA did not interfere with assay performance leading to false negative results.

DNA was independently extracted from the pellet and supernatant fractions of the BAL; no whole BAL was processed. In the case of the supernatant fraction, extraction started with 0.5 ml of the supernatant from the protein precipitation step onwards. For the pellet fraction, an additional bead beating step was included. Two milliliter sterile screw-cap tubes were loaded with silicon carbide sharps of sizes 0.1 mm and 1 mm (BioSpec Products, Inc., Bartlesville, Okla.) at a 1:1 ratio up to a volume equivalent to 250 µl. Yeast Cell Lysis™ solution at a volume of 550 µl and BAL pellet at 100-400 µl, or 200 µl of water as digest control, were added to the tube. The contents of the tube were homogenized in a FastPrep®-24 System (MP Biomedicals, Solon, Ohio) at 5 m/s for 60 s. Each tube was incubated at 65° C. for 45 min then kept on ice for 5 min.

MPC Protein Precipitation Reagent™ was added at a volume of 325 µl for pellet and 450 µl for supernatant processing. The tubes were vortexed for 10 s and centrifuged at 11,000 rcf for 10 min. The resulting supernatant was transferred to a new micro-centrifuge tube containing an equal volume of 100% isopropanol pre-cooled to −20° C. The contents of the tube were mixed thoroughly by inversion and incubated at −20° C. for 1 hour. Precipitated DNA was pelleted by centrifugation at 11,000 rcf for 10 min. The supernatant was removed and discarded. The pellet containing DNA was resuspended in 0.5 ml of pre-cooled (−20° C.) 70% ethanol and vortexed. The tube was then centrifuged at 11,000 rcf for 5 min. The supernatant was removed to a level just short of disturbing the pellet. The remaining volume of ethanol was allowed to evaporate by air drying for 5 min within the laminar flow hood. The pellet was resuspended in 100 µl of 0.1% Triton-X pre-warmed to 65° C. then incubated at room temperature for one minute with periodic gentle vortexing. The DNA was either used immediately for qPCR, stored at −20° C. overnight or at −80° C. for longer periods. If PCR inhibition was detected in the extracted samples, they were reprocessed from the protein precipitation step onwards (see FIG. 1).

Genomic DNA from fungi was extracted with an optimized MasterPure™ Yeast DNA Purification Kit (Epicentre® Biotechnologies, Madison, Wis.) in order to assess assay analytical sensitivity and specificity. Fungi were transferred into micro-centrifuge tubes from liquid media and centrifuged. Cell pellets were washed with 1 ml 1×PBS and centrifuged at 10,000 rcf for 3 min. The supernatant was discarded and cells resuspended in 500 µl Yeast Cell Lysis™ solution. The tube was vortexed at top speed for 10 s. The tube was incubated at 65° C. for 1 h and then kept on ice for 5 min. For filamentous fungi, the pellet was ground with a micropestle at the start and during the 65° C. incubation. Protein Precipitation Reagent™ was added at a volume of 400 µl alto the tube and vortexed for 10 s. The tube was centrifuged to pellet cellular debris at 11,000 rcf for 10 min. The supernatant was transferred to a new micro-centrifuge tube containing an equal volume of 100% isopropanol pre-cooled to −20° C. The contents of the tube were thoroughly mixed by inversion and incubated at −20° C. for 1 hr. Precipitated DNA was pelleted by centrifugation at 11,000 rcf for 10 min. The supernatant was removed and discarded. The pellet containing DNA was resuspended in pre-cooled (−20° C.) 1 ml of 70% ethanol and vortexed at maximum speed for 10 s. The tube was then centrifuged at 11,000 rcf for 5 min. This supernatant was removed to a level just short of disturbing the pellet. The remaining volume was allowed to evaporate by air drying for 5 min. The pellet was resuspended in 100 µl of 0.1% Triton-X pre-warmed to 65° C. and incubated at room temperature for 1 min with periodic gentle vortexing. The total nucleic acid in the extract was quantified using a UV spectrophotometer. For every 149 µg of total nucleic acid in the extract, 10 U of RiboShredder™ RNase Blend (Epicentre® Biotechnologies, Madison, Wis.) was used to remove RNA. RNA removal was confirmed by visualizing the pre- and post-treatment extract on a 1.5% agarose gel. DNA was quantified using a Qubit™ instrument and Quant-iT™ dsDNA HS Assay Kit (Invitrogen Corporation, Carlsbad, Calif.).

Quantitative PCR Assays

Quantitative PCR assays in this study were based on Taqman™ chemistry and an Applied Biosystems 7500™ real-time instrument was used for detection. To prevent contamination, each PCR master mix without additional water component was filtered through a Microcon YM-100 centrifugal filter unit with a MWCO of 100 kDa (Millipore Corporation, Billerica, Mass.) at 650 rcf for 25 min and 1500 rcf for an additional 5 min before use. The additional water was independently filtered with an Amicon Ultra-15 centrifugal filter unit with a MWCO of 30 kDa using. DNA-free micro-centrifuge tubes were used with the PCR set up (Eppendorf Biopur tubes. Eppendorf AG, Hamburg, Germany). No-template controls were run with each qPCR assay to monitor contamination. Each extracted BAL sample was run in duplicate reactions. Samples were interpreted as positive if both duplicates showed an increase in normalized relative florescence above the background and the multicomponent view demonstrated an increase in absolute florescence (as estimated by the 7500 System SDS software, Applied Biosystems).

(i) Internal Amplification Control (IAC) qPCR

The IAC qPCR was developed based on a 105 base template derived from the jellyfish aequorin gene which has a sequence of 5'-GCCTGGTGCAAAAATTGCTTATCAAAT-TGAACGGTCAATTGGAAGTGGCGGAA-GAACAGCTATTG CAAACGCCATCGCACAATACCAT-AAACACACTTGTCTTAG-3' (SEQ ID NO: 7) [24]. The amplicon was detected with a forward primer 5'-GCC TGG TGC AAA AAT TGC TTA TC-3' (SEQ ID NO: 3), reverse primer 5'-CTA AGA CAA GTG TGT TTA TGG TAT TG-3' (SEQ ID NO: 4), and probe labelled with fluorescein (Quasar670) and quenched with BHQ2: 5'-Quasar670 CTT CCG CCA CTT CCA ATT GAC CGT TCA BHQ2-3' (SEQ ID NO: 8; Biosearch Technologies, Novato, Calif.). The IAC was multiplexed with the *Aspergillus* targeted 18S qPCR and the human targeted 18S extraction control qPCR to monitor inhibition in every qPCR reaction. If inhibition as assessed by >2 cycle delay in the IAC threshold cycle was detected, DNA was re-purified and assayed again.

(ii) Extraction Control qPCR

Successful DNA extraction was confirmed in all samples with a qPCR targeting the human 18S rRNA gene with forward primer 5'-CTC TTA GCT GAG TGT CCC GC-3' (SEQ ID NO: 9), reverse primer 5'-CTT AAT CAT GGC CTC AGT TCC GA-3' (SEQ ID NO: 10), and probe labelled with fluorescein (FAM) and quenched with TAMRA: 5'-FAM CCG AGC CGC CTG GAT ACC GCA GCT A TAMRA-3' (SEQ ID NO: 11). Each 50 µl PCR mixture contained 1× TaqMan® Buffer A, 6 mM of MgCl$_2$, 1 mM of GeneAmp® dNTP Blend (12.5 mM with dUTP), 2.2 U of AmpliTaq Gold® DNA Polymerase, 0.05 U AmpErase® Uracil N-glycosylase (all from Applied Biosystems, Foster City, Calif.), 0.8 µM each of forward and reverse human targeted primers, 180 nM of human targeted probe, 0.24 µM each of forward and reverse of IAC primers, 180 nM of IAC probe, 0.002% of Triton-X 100, $10^5$ copies of IAC template and 5 µl of DNA.

The PCR cycling conditions included a Uracil N-glycosylase activation at 50° C. for 2 min, pre-melt at 95° C. for 10 min and then 38 cycles of 95° C. for 15 s (melt) and 65° C. for 65 s (annealing and extension). A standard curve for quantifying human DNA was generated using human genomic DNA (Roche Applied Sciences, Indianapolis, Ind.) with dilutions ranging from 10,000 to 1 pg.

Sham digest controls were negative for *Aspergillus* DNA, showing that no fungal contamination was evident in the DNA extraction reagents. No-template controls were also negative, showing that fungal DNA contamination was not detected in the PCR reagents.

(iii) *Aspergillus* Targeted 18S qPCR

The *Aspergillus* targeted qPCR amplified a 114 bp segment of the *Aspergillus* 18S rRNA gene with forward primer 5'-GAT AAC GAA CGA GAC CTC GG-3' (SEQ ID NO: 1), reverse primer 5'-AGA CCT GTT ATT GCC GCG C-3' (SEQ ID NO: 2) and probe 5'-FAM CTT AAA TAG CCC GGT CCG C BHQ-3' (SEQ ID NO: 5) with minor groove binding modification. Each 50 µl PCR mixture contained 1× TaqMan® Buffer A, 6 mM of MgCl$_2$, 1 mM of GeneAmp® dNTP Blend (12.5 mM with dUTP), 2.2 U of AmpliTaq Gold® DNA Polymerase, 0.05 U AmpErase® Uracil N-glycosylase (all from Applied Biosystems, Foster City, Calif.), 0.8 µM each of forward and reverse *Aspergillus* targeted primers, 200 nM of *Aspergillus* targeted probe, 0.4 µM each of forward and reverse of IAC primers, 190 nM of IAC probe, 0.002% of Triton-X 100, $10^5$ copies of IAC template and 5 µl of DNA. The PCR cycling conditions consisted of an Uracil N-glycosylase activation at 50° C. for 2 min, pre-melt at 95° C. for 10 min and then 45 cycles of 95° C. for 15 s (melt) and 65° C. for 65 s (annealing and extension). A standard curve for quantifying *Aspergillus* DNA was generated using *Aspergillus fumigatus* genomic DNA (ATCC #MYA-1163) dilutions ranging from 1000 pg to 30 fg. All positive *Aspergillus* qPCRs for the first 48 episodes were subjected to sequencing using Big Dye terminators and an Applied Biosystems capillary sequencer to confirm identity with the expected target.

Analytical Specificity Testing

The analytical specificity of the *Aspergillus* qPCR was assessed by testing 1000 pg of genomic DNA from 29 different fungal species spanning 15 genera grown in culture. The following clinically or phylogenetically relevant fungal pathogens were chosen: *Aspergillus fumigatus* (ATCC # MYA-1163), *Aspergillus oryzae* (ATCC #20719), *Aspergillus ustus* (ATCC #20063), *Aspergillus candidus* (ATCC #20022), *Aspergillus terreus* (ATCC #10070). *Aspergillus flavus* (ATCC #MYA-3631), *Candida albicans* (ATCC #90028), *Candida glabrata* (ATCC #90876), *Candida kefyr* (ATCC #28838), *Candida guilliermondii* (ATCC #90877),

*Candida lusitaniae* (ATCC #42720), *Candida dubliniensis* (ATCC #MYA-580), *Scedosporium apiospermum* (ATCC #28206), *Scedosporium prolificans* (ATCC #90468), *Paecilomyces variotti* (ATCC #10865), *Penicillium chrysogenum* (ATCC #10108), *Rhizopus oryzae* (ATCC #10260), *Rhodotorula glutinis* (ATCC #16726), *Absidia corymbifera* (ATCC #14058), *Fusarium solani* (ATCC #56480), *Mucor racemosus* (ATCC #42647), *Rhizomucor miehei* (ATCC #46345), *Cunninghamella bertholletiae* (ATCC #42155), *Trichosporon cutaneum* (ATCC #38300), *Candida parapsilosis* (clinical isolate), *Candida tropicalis* (clinical isolate), *Candida krusei* (clinical isolate), *Saccharomyces cerevisiae* (Novagen, Madison, Wis.), and *Cryptococcus neoformans* (ATCC #28958D-5). Cross-reactivity with 1 μg of human genomic DNA was also assessed.

Data Analysis

Quantitative PCR results were compared with clinical diagnoses based on the EORTC/MSG criteria. Sensitivity, specificity and positive and negative likelihood ratios with their associated 95% confidence intervals were calculated. The negative and positive predictive values (NPV and PPV) were also calculated for these sequentially obtained samples. These diagnostic parameters were also calculated for culture, histology and both culture and histology combined. A receiver-operating characteristic (ROC) analysis was done using a computer program written with MathWorks MATLAB® software to assess how changing qPCR detection threshold affects sensitivity and 1-specificity.

Example 2

Demographic Characteristics of the Patient Population

Of the 81 subjects with pneumonia or pulmonary nodules studied, 60 (74.1%) underwent hematopoietic cell transplantation and the remainder of the subjects had a diagnosis of leukaemia, lymphoma, or another neoplastic condition (see Table 1).

TABLE 1

Demographic Characteristics in 81 Subjects

| Characteristic | Patients with: | | |
| --- | --- | --- | --- |
| | Proven or Probable IPA | No IPA | Total |
| Sex: | | | |
| Male | 7 | 42 | 49 |
| Female | 6 | 26 | 32 |
| Age (years): | | | |
| Median | 60.91 | 50.40 | 53.68 |
| Range | 37.09-73.39 | 17.97-72.45 | 17.97-73.39 |
| Transplant type: | | | |
| Allogeneic | 6 | 40 | 46 |
| Autologous | 2 | 12 | 14 |
| Non-Transplant | 5 | 16 | 21 |
| Underlying disease: | | | |
| ALL (Acute Lymphoblastic Leukemia) | 0 | 8 | 8 |
| AML (Acute Myeloid Leukemia) | 4 | 12 | 16 |
| AMM (Agnogenic Myeloid Metaplasia) | 1 | 2 | 3 |
| AMML (Acute Myelomonocytic Leukemia) | 0 | 4 | 4 |

TABLE 1-continued

Demographic Characteristics in 81 Subjects

| Characteristic | Patients with: | | |
| --- | --- | --- | --- |
| | Proven or Probable IPA | No IPA | Total |
| CLL (Chronic Lymphocytic Leukemia) | 0 | 3 | 3 |
| CML (Chronic Myeloid Leukemia) | 0 | 7 | 7 |
| HD (Hodgkin's Disease) | 1 | 6 | 7 |
| NHL (Non Hodgkin's Lymphoma) | 1 | 8 | 9 |
| MM (Multiple Myeloma) | 3 | 4 | 7 |
| RA (Refractory Anemia) | 1 | 6 | 7 |
| Other | 2 | 8 | 10 |

Accordingly, the study population represents a group of patients at very high risk for invasive aspergillosis based on risk factors such as underlying malignancy, neutropenia, and use of steroids.

Example 3

Analytical Sensitivity and Specificity of the qPCR Assays

The *Aspergillus* qPCR standard curve of genomic *Aspergillus* DNA consistently yielded $R^2$ (goodness-of-fit) values>0.98, which enabled quantification. The *Aspergillus* qPCR could reliably detect down to a threshold cycle (Ct) of 41 which is approximately equivalent to 1 fg of *Aspergillus* genomic DNA or a single copy of the target 18S rRNA gene.

The analytical sensitivity of the human 18S rRNA gene targeted extraction control qPCR was tested with human genomic DNA. The extraction control qPCR could reliably detect down to 37 Ct which is approximately equivalent to 1 pg of human genomic DNA or one-third of a human genome or 88 copies of the target 18S rRNA gene. The standard curve of human genomic DNA consistently yielded $R^2$ (goodness-of-fit) values>0.98 for the human 18S rRNA gene qPCR, which enabled quantification of amounts of cellular material in BAL fluid.

The extraction control qPCR qualitatively confirmed successful DNA extraction and estimated the amount of human genomic DNA present in all 144 BAL samples. The median amount of human genomic DNA per BAL pellet was 2.08 pg/pellet (52.1 ng per qPCR reaction) with a range of 9 ng to 58.8 μg per pellet. The amount of genomic DNA in the supernatant fraction was relatively low at a median of 88.8 ng/ml of BAL supernatant and had a range of 0.05 ng to 22.43 μg per ml BAL supernatant.

To determine the specificity of the *Aspergillus* qPCR, 1 μg of human DNA and 1000 pg of fungal DNA from 29 species spanning 15 genera were tested in the *Aspergillus* qPCR assay. Cross-reactivity studies of the *Aspergillus* qPCR with human DNA revealed that 10 fg of *Aspergillus* DNA could be successfully amplified in the presence of 1 μg of human DNA per reaction. In actual BAL clinical samples, as little as 20 fg of *Aspergillus* DNA was detected in the presence of 550 ng of human DNA per reaction.

False positives due to cross-reactivity of non-*Aspergillus* fungi are substantially reduced with the presently disclosed *Aspergillus* qPCR assay. Extensive analytical specificity testing demonstrated that of the 23 non-*Aspergillus* fungal species tested, the present *Aspergillus* qPCR assay exhibited cross-reactivity with only *Penicillium chrysogenum* (a/k/a

*Penicillium notatum*) and *Paecilomyces variotii*. *P. chrysogenum* is a ubiquitous fungus closely related to *A. fumigatus*. It is rarely associated with human opportunistic infections. *P. variotii* is an opportunistic human pathogen, but voriconazole, which is considered first line therapy targeting *Aspergillus* species, is also active against *P. variotii*. Thus the clinical ramifications of incorrectly calling a *Paecilomyces* infection an *Aspergillus* infection are likely to be small. The galactomannan antigen assay for diagnosis of aspergillosis is also susceptible to false positive results due to cross-reactivity with antigens from these two fungal species [10].

These results demonstrate that very small quantities of *Aspergillus* DNA (<1 genome) can be detected in a background of large amounts of human DNA ($10^9$ fold excess DNA by mass) using this assay. BAL samples from the first 48 episodes consisting of 10 true positives where an amplification product was detected were sequenced and confirmed to have DNA that matched the *Aspergillus* genus for each episode. Based on this high concordance rate sequencing was not performed for the subsequent 46 episodes.

Example 4

Internal Amplification Control Analysis of PCR Inhibition

It has been suggested that an internal amplification control (IAC) is critical for assessing PCR inhibition in every sample to rule out inhibition as a cause for false-negatives (FNs) [20, 32]. Very few studies related to fungal PCR diagnostics analyzing BAL fluid have incorporated an IAC [33, 34], however, and only one of those studies focused on *Aspergillus* detection in BAL.

The present example discloses the use of an IAC that was a truncated version of an exogenous DNA template derived from the jellyfish aequorin gene previously used in PCR studies for the diagnosis of cytomegalovirus disease [24]. Known amounts of IAC template introduced in the multiplexed qPCR mastermix enabled reliable quantification of inhibition in the *Aspergillus* or extraction control qPCRs. Because the TAC was added during the qPCR stage, it was unaffected by other variables of the process (like DNA extraction) and therefore it exclusively monitored inhibition in qPCR. In addition, the multiplexed IAC amplified with primers and probe independent from the target and its reaction kinetics were optimized such that it did not affect the analytical sensitivity of the target qPCR assay (as confirmed by the positive *A. fumigatus* standards in each experiment).

The IAC qPCR detected inhibition in 7.6% (11 out of 144) of the BAL samples. Re-extraction of DNA eliminated PCR inhibition in all samples without significant losses of DNA. Therefore, the IAC ruled out qPCR inhibition as a cause for FNs. Moreover, the IAC qPCR multiplexed with the *Aspergillus* qPCR assay did not manifest any inhibition even in the presence of human genomic DNA as high as 1.5 ng per reaction suggesting that the IAC was monitoring for qPCR inhibition independent of the large quantities of human genomic DNA found in extracted BAL fluid.

The IAC signal in the no-template controls was compared with the IAC signal of the BAL sample. A delay of 2 Ct (equivalent to a 3-fold change in quantity) or greater in duplicate qPCR reactions was used as a cut-off to classify a sample as having significant qPCR inhibition. The IAC multiplexed with the *Aspergillus* 18S was more useful in detecting inhibition when compared with the IAC multiplexed with the extraction control assay. This is because the IAC signal in the extraction control was at a severe competitive disadvantage due to the large amounts of human DNA present in each sample. The IAC multiplexed with the *Aspergillus* 18S assay detected significant inhibition in 11 samples. Inhibition in all these samples was overcome by re-extraction from the protein precipitation step onwards without significant loss of DNA as assessed by the extraction control qPCR (FIG. 1). When the re-extracted samples were assayed again, the IAC did not detect any inhibition.

Example 5

Determination of the Optimal Fraction for Detection of *Aspergillus* DNA in BAL Fluid After processing 66 BAL fluid samples from 48 episodes of pneumonia, data analysis was done to evaluate which fraction of BAL fluid contains the most *Aspergillus* DNA. Ten episodes were categorized as proven or probable IPA in this cohort of 48 episodes; within these 10 episodes, *Aspergillus* DNA was detected in 7 of 10 for the pellet fraction and in only 4 of 10 for the supernatant fraction. All positive supernatant fractions also had a positive pellet fraction.

Of all qPCR positive BALs, an average of 98.3±3.8% of total *Aspergillus* DNA from both fractions was seen in the pellet. Analysis of BAL pellet and supernatant results together conferred sensitivity and specificity identical to that of BAL pellet alone. Although the supernatant fraction had low sensitivity (40%), it was highly specific in identifying episodes with proven or probable IPA (specificity 100%). Since BAL fluid supernatant did not appear to add meaningfully to the diagnostic yield, further analysis of BAL samples focused on analysis of BAL pellet fractions.

Example 6

Diagnostic Utility of the *Aspergillus* qPCR, Culture, and Histology

BAL fluid from 94 episodes of pneumonia in 81 patients was analyzed. Thirteen episodes were categorized as proven or probable IPA using Mycoses Study Group criteria. The pellet and the supernatant fractions of the BAL were separately assayed. A successful extraction was confirmed with a human 18S rRNA gene qPCR. Inhibition in each qPCR was measured using an exogenous DNA based internal amplification control (IAC). The presence of DNA from pathogens in the *Aspergillus* genus was detected using qPCR targeting fungal 18S rRNA gene.

Human 18S rRNA gene qPCR confirmed successful DNA extraction of all samples. IAC detected some degree of initial inhibition in 11 samples. When culture was used to diagnose IPA, the sensitivity and specificity were 84.5% and 100%, respectively. Receiver-operating characteristic analysis of qPCR showed that a cutoff of 13 fg of *Aspergillus* genomic DNA generated a sensitivity, specificity, positive and negative predictive value of 77%, 88%, 50%, 96% respectively. BAL pellet and supernatant analyzed together resulted in sensitivity and specificity similar to BAL pellet alone. Some patients did not meet standard criteria for IPA, but had consistently high levels of *Aspergillus* DNA in BAL fluid by qPCR.

The *Aspergillus* qPCR assay detected *Aspergillus* DNA in 76.9% of subjects with proven or probable IPA when the concentrated BAL fluid pellet fraction was used for diagnosis. Use of both extraction and amplification controls provided optimal quality control for interpreting qPCR results and therefore may increase our understanding of the true potential of qPCR for the diagnosis of IPA.

Figure 2:
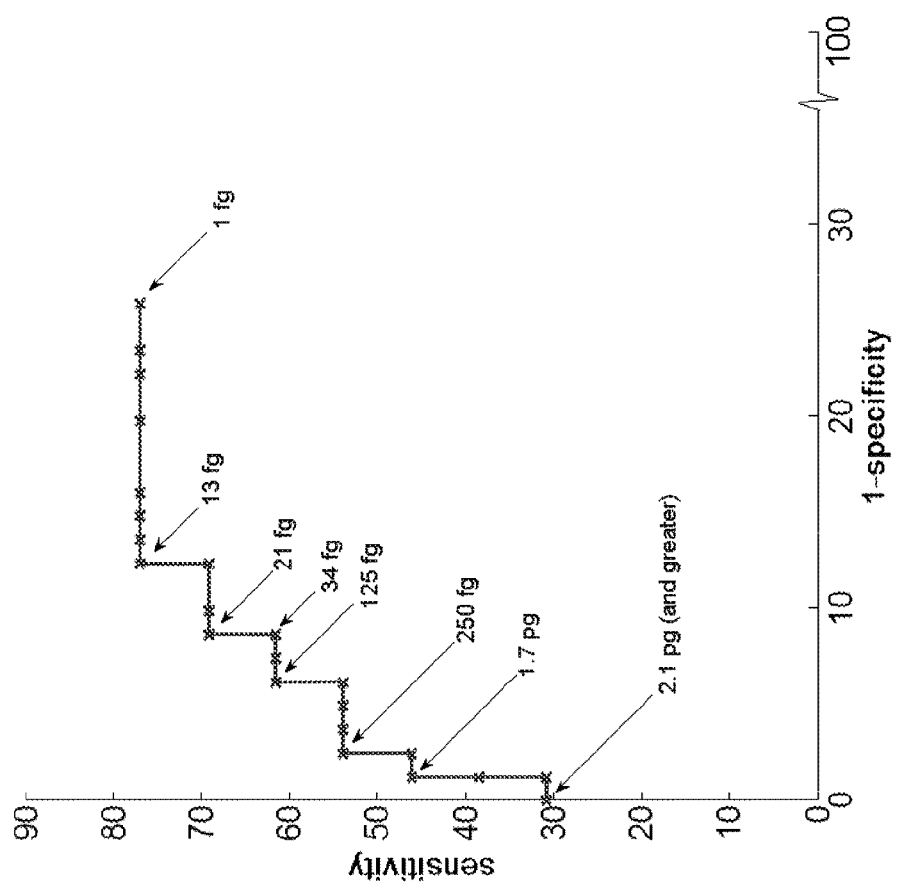
FIG. 2 is a receiver-operating characteristic (ROC) curve depicting sensitivity versus 1-specificity of *Aspergillus* qPCR assay as a function of detection threshold of fungal burden in the BAL pellet (1 pg=1000 fg). One genome of *A. fumigatus* corresponds to about 30-fg of genomic DNA and is estimated to have 28 copies of the target 18S rRNA gene

Table 2 summarizes the key diagnostic parameters of the qPCR assay, culture, and histology in detecting the presence of *Aspergillus* in BAL fluid. A ROC curve of the *Aspergillus* qPCR assay depicted diagnostic sensitivity versus 1-specificity as a function of detection threshold of fungal burden (e.g., femtograms of DNA). This was useful in identifying the threshold of detection with an optimal trade-off between diagnostic sensitivity and specificity. ROC analysis of qPCR showed that a cut-off of 13 fg of *Aspergillus* genomic DNA per BAL pellet (corresponding to approximately 41 cycles) generated good sensitivity and specificity (FIG. 2). Based on this cut-off, the *Aspergillus* qPCR assay detected 10 of 13 episodes with proven or probable IPA (sensitivity 76.9%) and 8 out of 81 episodes without proven or probable IPA (specificity 90.1%). The positive and negative predictive values were 58% and 94%. The lower PPV reflects the relatively low prevalence of IPA when analyzed on a per episode basis. A high NPV is useful as it suggests that a patient is unlikely to have IPA if the test is negative, and this may spare the patient from receiving unnecessary antifungal treatment that was started empirically, though these results do not rule out infection with another fungus. For all BALs with any *Aspergillus* DNA detected by qPCR, the median quantity of *Aspergillus* DNA was 173 fg with a range of 4 fg to >1500 pg per pellet.

ogy combined (Table 2). In contrast to culture, however, qPCR results can be generated in one day. Although culture was equally sensitive in detecting IPA in this study, it should be noted that this result probably reflects the critical role that cultivation played in defining subjects with IPA using EORTC/MSG criteria in this study. Several studies in the past have reported the sensitivity of BAL culture to be relatively low (<50%) [4, 7, 8]. Of the 13 episodes with proven or probable IPA, culture and *Aspergillus* qPCR (with a 13 fg detection threshold) were concurrently positive for 8 episodes. There were 2 episodes when culture was negative and qPCR was positive and 3 episodes when culture was positive and qPCR negative. In addition, qPCR was always positive when histology was positive. This implies that when qPCR is conjunctively used with culture, sensitivity of detecting IPA could approach 100%, though much larger numbers of samples will be needed to define the true sensitivity and specificity of the qPCR assay. The significant correlation of fungal burden estimated by qPCR and the CFUs reported by culture tests implies qPCR is highly likely to be positive when culture and/or histology are positive. This result is in concordance with several published studies [15, 18, 34, 37].

TABLE 2

Summary of Diagnostic Performance in the Detection of IPA

| Diagnostic assay | BAL fraction | Sensitivity (%) | Specificity (%) | Positive Predictive Value (%) | Negative Predictive Value (%) | Positive Likelihood Ratio | Negative Likelihood Ratio |
|---|---|---|---|---|---|---|---|
| qPCR, 13 fg | pellet | 76.9 (50-92) | 87.7 (79-93) | 58 | 94 | 8.63 (3.2-11.9) | 0.33 (0.1-0.7) |
| qPCR, 13 fg | supernatant | 40 (17-69) | 97.3 (86-99) | 80.02 | 85.70 | 14.8 (1.9-118.1) | 0.62 (0.37-1) |
| Culture | whole (unfractionated) | 84.6 (58-96) | 100 (95-100) | 100 | 97.6 | infinity | 0.15 (0.04-0.6) |
| Histology | whole (unfractionated) | 53.8 (29-77) | 100 (95-100) | 100 | 93.1 | infinity | 0.46 (0.3-0.8) |
| Culture or Histology | whole (unfractionated) | 85.7 (60-96) | 100 (95-100) | 100 | 97.7 | infinity | 0.99 (0.04-0.5) |

The range of values within brackets are estimated for a confidence interval of 95%. Thirteen femtograms (fg) of *Aspergillus* DNA was selected as threshold for a positive PCR assay result, and is approximately equal to ⅓ of an *Aspergillus fumigatus* genome. The supernatant fraction of the BAL was assayed for the first 48 episodes.

BAL culture was somewhat more sensitive than qPCR in detecting IPA (sensitivity 84.6%) and had high specificity (100%). Histology on the other hand was less sensitive (53.8%), but had high specificity (100%). When culture and histology were used in combination, the sensitivity increased slightly to 85.7% and specificity remained at 100%. There was only a single episode with proven or probable IPA in which the histology was positive when the culture was negative. For this episode, the *Aspergillus* qPCR was convincingly positive with 2 pg of *Aspergillus* DNA found in the pellet.

Two episodes with proven or probable IPA which were culture positive were not positive for qPCR or histology. For these episodes, the culture was positive for *Aspergillus* at a single CFU level. One episode with proven or probable IPA showed no evidence of *Aspergillus* by culture or histology and was also negative by *Aspergillus* qPCR—this subject had a lung biopsy shortly after BAL fluid acquisition that confirmed IPA. The Pearson correlation coefficient (r) calculated between the fungal burden estimated by qPCR and the number of colony forming units detected by culture in BAL was 0.93 (95% C.I. of 0.85-0.97, df=25, p<0.01), suggesting a strong relationship between these two independent measures of fungal burden. The 95% confidence intervals were estimated based on the Fisher r-to-z transformation.

The data presented herein demonstrated that quantitative PCR was about as sensitive as culture or culture with histol- The range of values within brackets are estimated for a confidence interval of 95%. Thirteen femtograms (fg) of *Aspergillus* DNA was selected as threshold for a positive PCR assay result, and is approximately equal to ⅓ of an *Aspergillus fumigatus* genome. The supernatant fraction of the BAL was assayed for the first 48 episodes.

Tables 3 and 4 show information about the false positive and false negative cases as identified by qPCR. Some patients did not meet standard criteria for IPA, but had consistently high levels of *Aspergillus* DNA in BAL fluid by qPCR based on repeated assays (Table 3). Since the no-template controls and digest controls were consistently negative, the FPs could not be directly attributed to contamination from DNA extraction or qPCR reagents. All 3 FNs were negative for histology (Table 4).

One (patient #9) was also negative for culture and the other two FNs (patient #10 and 11) had positive culture values reported at a level of 1 CFU. These low or negative culture values could potentially reflect lower fungal burden in the BALs which could impact detection by qPCR. The IAC analysis ruled out PCR inhibition as a cause for FNs. In addition, the human genomic DNA amounts in the BAL pellets of FN samples were well within the tested limits of cross-reactivity with amplification by *Aspergillus* qPCR and hence inhibition due to human genomic DNA overload does not appear to be a factor affecting FN results. FN patient #9 had the lowest amount of human genomic DNA per reaction of the entire study at 0.23 ng (Table 4). This could imply that enough cellular mass was not sampled during bronchoscopy which could in turn affect the chance of sampling fungal cells from the potential site of infection.

Some patients (7) did not meet standard criteria for IPA, but had consistently high levels of *Aspergillus* DNA in BAL fluid by qPCR, as documented by repeated detection in multiple qPCR assays performed on different days (Table 3). These cases may be false positives due to fungal colonization of the airways, fungal contamination at the time of BAL collection, or true positives indicative of shortcomings in the EORTC/MSG criteria for defining IPA. Several of these patients had a diagnosis of idiopathic pneumonia syndrome or related pulmonary conditions after hematopoietic cell transplantation and were treated with mould-active antifungal medications empirically, thus the diagnosis of IPA cannot be completely excluded despite the absence of formal criteria for IPA. On the other hand, other patients did not receive mould-active antifungal therapy and did not appear to develop sequelae of IPA despite absence of treatment, suggesting that these episodes are definite false positives.

Among the 3 patients with false negative results, one had no evidence of *Aspergillus* in the original BAL sample using any diagnostic method, but proved to have IPA based on a subsequent lung biopsy. This false negative sample had the lowest amount of cellular material of all the BALs processed in this study which may reflect inadequate sampling of the lung segment at the time of bronchoscopy with BAL. Two patients with false negative PCRs for *Aspergillus* had 1 CFU of *Aspergillus* detected in BAL fluid by culture. This failure to detect *Aspergillus* DNA in the BAL fluid from these 2 subjects may reflect the low burden of fungal organisms, or may reflect the fact that these culture results are false positives (laboratory contamination), leading to improper classification using EORTC/MSG criteria.

TABLE 3

| | False Positive Cases | | | |
|---|---|---|---|---|
| Pt. | *Aspergillus* DNA (fg/pellet) | BAL Culture | Clinical Diagnosis | Computed tomography scan results and other clinical information |
| 1 | 5230 | negative | DAH | Organizing pneumonia on lung biopsy with pulmonary hemorrhage; treated with ambisome empirically; No IPA at autopsy |
| 2 | 230 | negative | BOOP | Bilateral patchy opacities; no mould active antifungal therapy given |
| 3 | 60 | negative | Unknown | Nodular right middle lobe infiltrate treated with levofloxacin; exposure to hay |
| 4 | 340 | negative | IPA | Multiple bilateral nodules; treated as IPA with voriconazole + caspofungin |
| 5 | 320 | negative | DAH | Bilateral geographic grounds glass opacities; treated with caspofungin |
| 6 | 80 | negative | BOOP | Numerous bilateral ground glass opacities; treated with prednisone but no antifungal therapy |
| 7 | 170 | negative | Influenza pneumonia/PCP | Left lung infiltrates; no antifungal therapy except for Pneumocystis |

Additional information about false positive (FP) cases as identified by qPCR. Pt.: patient; BOOP: Bronchiolitis obliterans with organizing pneumonia; DAH: Diffuse alveolar hemorrhage; PCP: Pneumocystis pneumonia.

TABLE 4

| | | False Negative Cases | | | |
|---|---|---|---|---|---|
| Pt. | BAL Culture | BAL Histology | Clinical Diagnosis | Human DNA (ng per reaction) | CT scan results and other clinical information |
| 8 | negative | negative | IPA | 0.23 from 1 BAL | No evidence of IPA in BAL; patchy bilateral infiltrates; lung biopsy 1 week later confirmed IPA by culture and histology |
| 9 | positive | negative | IPA DAH *Staphylococcus* pneumonia | 33 and 72.5 from 2 BALs | 1 CFU *A. fumigatus* in BAL fluid; patchy nodular infiltrates on CT; on ambisome for 10 days prior to bronchoscopy |
| 10 | positive | negative | IPA *Legionella* CMV pneumonia | 10 to 218 from 4 BALs | 1 CFU *A. niger* in BAL with CT scan showing halo sign, IPA confirmed at autopsy |

Additional information about false negative (FN) cases as identified by qPCR. Pt.: patient; DAH: Diffuse alveolar hemorrhage; CMV: Cytomegalovirus.

Additional information about false negative (FN) cases as identified by qPCR. Pt.: patient: DAH: Diffuse alveolar hemorrhage; CMV: Cytomegalovirus.

REFERENCES

[1] B. H. Segal and T. J. Walsh, "Current approaches to diagnosis and treatment of invasive aspergillosis," *Am J Respir Crit. Care Med*, vol. 173, pp. 707-17, 2006.

[2] M. M. McNeil, S. L. Nash, R. A. Hajjeh, M. A. Phelan, L. A. Conn, B. D. Plikaytis, and D. W. Warnock, "Trends in Mortality Due to Invasive Mycotic Diseases in the United States, 1980-1997," *Clinical Infectious Diseases*, vol. 33, pp. 641-647, 2001.

[3] P. Munoz, J. Guinea, and E. Bouza, "Update on invasive pulmonary aspergillosis: clinical and diagnostic aspects," *Clin Microbial Infect*, vol. 12 Suppl 7, pp. 24-39, 2006.

[4] F. Reichenberger, J. M. Habicht, A. Gratwohl, and M. Tamm, "Diagnosis and treatment of invasive pulmonary aspergillosis in neutropenic patients," *Eur Respir J*, vol. 19, pp. 743-55, 2002.

[5] J. P. Latge, "*Aspergillus fumigatus* and aspergillosis," *Clin Microbiol Rev*, vol. 12, pp. 310-50, 1999.

[6] F. Reichenberger, J. Habicht, P. Matt, R. Frei, M. Soler, C. T. Bolliger, P. Dalquen, A. Gratwohl, and M. Tamm, "Diagnostic yield of bronchoscopy in histologically proven invasive pulmonary aspergillosis," *Bone Marrow Transplant*, vol. 24, pp. 1195-9, 1999.

[7] H. Levy, D. A. Horak, B. R. Tegtmeier, S. B. Yokota, and S. J. Forman, "The value of bronchoalveolar lavage and bronchial washings in the diagnosis of invasive pulmonary aspergillosis," *Respir Med*, vol. 86, pp. 243-8, 1992.

[8] H. Saito, E. J. Anaissie, R. C. Morice, R. Dekmezian, and G. P. Bodey, "Bronchoalveolar lavage in the diagnosis of pulmonary infiltrates in patients with acute leukemia," *Chest*, vol. 94, pp. 745-9, 1988.

[9] O. Adam, A. Auperin, F. Wilquin, J. H. Bourhis, B. Gachot, and E. Chachaty, "Treatment with piperacillin-tazobactam and false-positive *Aspergillus* galactomannan antigen test results for patients with hematological malignancies," *Clin Infect Dis*, vol. 38, pp. 917-20, 2004.

[10] V. R. Aquino. L. Z. Goldani, and A. C. Pasqualotto. "Update on the contribution of galactomannan for the diagnosis of invasive aspergillosis," *Mycopathologia*, vol. 163, pp. 191-202, 2007.

[11] A. Kedzierska, P. Kochan, A. Pietrzyk, and J. Kedzierska, "Current status of fungal cell wall components in the immunodiagnostics of invasive fungal infections in humans: galactomannan, mannan and (1->3)-beta-D-glucan antigens," *Eur J Clin Microbiol Infect Dis*, vol. 26, pp. 755-66, 2007.

[12] F. F. Tuon, "A systematic literature review on the diagnosis of invasive aspergillosis using polymerase chain reaction (PCR) from bronchoalveolar lavage clinical samples," *Rev Iberoam Micol*, vol. 24, pp. 89-94, 2007.

[13] D. Buchheidt, C. Baust, H. Skladny, J. Ritter, T. Suedhoff, M. Baldus, W. Seifarth, C. Leib-Moesch, and R. Hehlmann, "Detection of *Aspergillus* species in blood and bronchoalveolar lavage samples from immunocompromised patients by means of 2-step polymerase chain reaction: clinical results," *Clin Infect Dis*, vol. 33, pp. 428-35, 2001.

[14] M. P. Hayette, D. Vaira, F. Susin, P. Boland, G. Christiaens, P. Melin, and P. De Mol, "Detection of *Aspergillus* species DNA by PCR in bronchoalveolar lavage fluid," *J Clin Microbiol*, vol. 39, pp. 2338-40, 2001.

[15] B. Musher, D. Fredricks, W. Leisenring, S. A. Balajee, C. Smith, and K. A. Marr, "*Aspergillus* galactomannan enzyme immunoassay and quantitative PCR for diagnosis of invasive aspergillosis with bronchoalveolar lavage fluid, " *J Clin Microbiol*, vol. 42, pp. 5517-22, 2004.

[16] I. Raad, H. Hanna, A. Huaring a, D. Sumoza, R. Hachem, and M. Albitar, "Diagnosis of invasive pulmonary aspergillosis using polymerase chain reaction-based detection of *aspergillus* in BAL," *Chest*, vol. 121, pp. 1171-6, 2002.

[17] K. Rantakokko-Jalava, S. Laaksonen, J. Issakainen, J. Vauras, J. Nikoskelainen, M. K. Viljanen, and J. Salonen, "Semiquantitative detection by real-time PCR of *Aspergillus fumigatus* in bronchoalveolar lavage fluids and tissue biopsy specimens from patients with invasive aspergillosis," *J Clin Microbiol*, vol. 41, pp. 4304-11, 2003.

[18] M. Sanguinetti, B. Posteraro, L. Pagano, G. Pagliari, L. Fianchi, L. Mele, M. La Sorda, A. Franco, and G. Fadda, "Comparison of real-time PCR, conventional PCR, and galactomannan antigen detection by enzyme-linked immunosorbent assay using bronchoalveolar lavage fluid samples from hematology patients for diagnosis of invasive pulmonary aspergillosis," *J Clin Microbiol*, vol. 41, pp. 3922-5, 2003.

[19] B. Spiess, D. Buchheidt, C. Baust, H. Skladny, W. Seifarth, U. Zeilfelder, C. Leib-Mosch, H. Morz, and R. Hehlmann, "Development of a LightCycler PCR assay for detection and quantification of *Aspergillus fumigatus* DNA in clinical samples from neutropenic patients," *J Clin Microbiol*, vol. 41, pp. 1811-8, 2003.

[20] R. R. Paterson, "Internal amplification controls have not been employed in fungal PCR hence potential false negative results," *J Appl Microbiol*, vol. 102, pp. 1-10, 2007.

[21] J. Loeffler, H. Hebart, R. Bialek, L. Hagmeyer, D. Schmidt, F. P. Serey, M. Hartmann, J. Eucker, and H. Einsele, "Contaminations occurring in fungal PCR assays," *J Clin Microbiol*, vol. 37, pp. 1200-2, 1999.

[22] S. Bretagne, "Molecular diagnostics in clinical parasitology and mycology: limits of the current polymerase chain reaction (PCR) assays and interest of the real-time PCR assays," *Clin Microbiol Infect*, vol. 9, pp. 505-11, 2003.

[23] S. Ascioglu, J. H. Rex, B. de Pauw, J. E. Bennett, J. Bille, F. Crokaert, D. W. Denning, J. P. Donnelly, J. E. Edwards, Z. Erjavec, D. Fiere, O. Lortholary, J. Maertens, J. F. Meis, T. F. Patterson, J. Ritter, D. Selleslag, P. M. Shah, D. A. Stevens, and T. J. Walsh, "Defining opportunistic invasive fungal infections in immunocompromised patients with cancer and hematopoietic stem cell transplants: an international consensus," *Clin Infect Dis*, vol. 34, pp. 7-14, 2002.

[24] A. P. Limaye, M. L. Huang, W. Leisenring, L. Stensland, L. Corey, and M. Boeckh, "Cytomegalovirus (CMV) DNA load in plasma for the diagnosis of CMV disease before engraftment in hematopoietic stem-cell transplant recipients," *J Infect Dis*, vol. 183, pp. 377-82, 2001.

[25] R. B. Ferns, "Evaluation of the role of real-time PCR in the diagnosis of invasive aspergillosis," *Leuk Lymphoma*, vol. 47, pp. 15-20, 2006.

[26] C. Y. Ou, J. L. Moore, and G. Schochetman, "Use of UV irradiation to reduce false positivity in polymerase chain reaction," *Biotechniques*, vol. 10, pp. 442, 444, 446, 1991.

[27] J. M. Wages, Jr., D. Cai, and A. K. Fowler, "Removal of contaminating DNA from PCR reagents by ultrafiltration," *Biotechniques*, vol. 16, pp. 1014-7, 1994.

[28] J. A. Jordan and M. B. Durso, "Comparison of 16S rRNA gene PCR and BACTEC 9240 for detection of neonatal bacteremia," *J Clin Microbiol*, vol. 38, pp. 2574-8, 2000.

[29] J. Loffler, H. Hebart, U. Schumacher, H. Reitze, and H. Einsele, "Comparison of different methods for extraction of DNA of fungal pathogens from cultures and blood," *J Clin Microbiol*, vol. 35, pp. 3311-2, 1997.

[30] D. N. Fredricks, C. Smith, and A. Meier, "Comparison of six DNA extraction methods for recovery of fungal DNA as assessed by quantitative PCR," *J Clin Microbiol*, vol. 43, pp. 5122-8, 2005.

[31] L. J. Griffiths, M. Anyim, S. R. Doffman, M. Wilks, M. R. Millar, and S. G. Agrawal, "Comparison of DNA extraction methods for *Aspergillus fumigatus* using real-time PCR," *J Med Microbiol*, vol. 55, pp. 1187-91, 2006.

[32] J. Hoorfar, B. Malorny, A. Abdulmawjood, N. Cook, M. Wagner, and P. Fach, "Practical considerations in design of internal amplification controls for diagnostic PCR assays," *J Clin Microbiol*, vol. 42, pp. 1863-8, 2004.

[33] A. M. Caliendo, P. L. Hewitt, J. M. Allega, A. Keen, K. L. Ruoff, and M. J. Ferraro, "Performance of a PCR assay for detection of *Pneumocystis carinii* from respiratory specimens," *J Clin Microbiol*, vol. 36, pp. 979-82, 1998.

[34] S. Bretagne, J. M. Costa, A. Marmorat-Khuong, F. Poron, C. Cordonnier, M. Vidaud, and J. Fleury-Feith, "Detection of *Aspergillus* species DNA in bronchoalveolar lavage samples by competitive PCR," *J Clin Microbiol*, vol. 33, pp. 1164-8, 1995.

[35] R. Herbrecht, V. Letscher-Bru, C. Oprea, B. Lioure, J. Waller, F. Campos, O. Villard, K. L. Liu, S, Natarajan-Ame, P. Lutz, P. Dufour, J. P. Bergerat, and E. Candolfi, "*Aspergillus* galactomannan detection in the diagnosis of invasive aspergillosis in cancer patients," *J Clin Oncol*, vol. 20, pp. 1898-906, 2002.

[36] C. D. Pfeiffer, J. P. Fine, and N. Safdar, "Diagnosis of invasive aspergillosis using a galactomannan assay: a meta-analysis," *Clin Infect Dis*, vol. 42, pp. 1417-27, 2006.

[37] C. Spreadbury, D. Holden, A. Aufauvre-Brown, B. Bainbridge, and J. Cohen, "Detection of *Aspergillus fumigatus* by polymerase chain reaction," *J Clin Microbiol*, vol. 31, pp. 615-21, 1993.

---

What is claimed is:

1. A primer set for the diagnosis of invasive pulmonary aspergillosis (IPA), said primer set consisting essentially of a forward primer and a reverse primer wherein said forward primer and said reverse primer are capable of amplifying a region of one or more *Aspergillus* spp gene(s) from each of *Aspergillus fumigatus, Aspergillus oryzae, Aspergillus ustus, Aspergillus candidus, Aspergillus terreus*, and *Aspergillus flavus* in the presence of human DNA.

2. The primer set of claim 1 wherein one of said *Aspergillus* spp gene(s) is a ribosomal RNA (rRNA) gene.

3. The primer set of claim 2 wherein one of said *Aspergillus* spp gene(s) is an 18S rRNA gene.

4. The primer set of claim 3 wherein said forward primer comprises the nucleotide sequence 5'-GAT AAC GAA CGA GAC CTC GG-3' (SEQ ID NO: 1) and said reverse primer comprises the nucleotide sequence 5'-AGA CCT GTT ATT GCC GCG C-3' (SEQ ID NO: 2).

5. A kit for the diagnosis of invasive pulmonary aspergillosis (IPA), said kit comprising:
   (1) a primer set consisting essentially of a forward primer and a reverse primer wherein said forward primer and said reverse primer are capable of generating a PCR amplicon from a region of one or more *Aspergillus* spp gene(s) from each of *Aspergillus fumigatus, Aspergillus oryzae, Aspergillus ustus, Aspergillus candidus, Aspergillus terreus*, and *Aspergillus flavus* in the presence of human DNA and
   (2) a probe capable of hybridizing to said PCR amplicon.

6. The kit of claim 5 further comprising an internal amplification control (IAC) primer set comprising a second forward primer and a second reverse primer wherein said second forward primer and said second reverse primer are capable of generating a PCR amplicon from a region of a second gene having a nucleotide sequence that is unrelated to said one or more *Aspergillus* spp gene(s).

7. The kit of claim 6 wherein said second forward primer comprises the nucleotide sequence 5'-GCC TGG TGC AAA AAT TGC TTA TC-3' (SEQ ID NO: 3) and wherein said second reverse primer comprises the nucleotide sequence 5'-CTA AGA CAA GTG TGT TTA TGG TAT TG-3' (SEQ ID NO: 4).

8. A quantitative PCR method for the diagnosis of invasive pulmonary aspergillosis (IPA) in a patient sample, said method comprising the steps of:
   (a) collecting a cell fraction from said sample,
   (b) extracting DNA from said cell fraction,
   (c) carrying out a quantitative PCR (qPCR) reaction on the patient sample with a primer set consisting essentially of a forward primer and a reverse primer wherein said primer set permits the generation of an amplicon that includes a region of an *Aspergillus* spp. gene from each of *Aspergillus fumigatus, Aspergillus oryzae, Aspergillus ustus, Aspergillus candidus, Aspergillus terreus*, and *Aspergillus flavus* in the presence of human DNA, and
   (d) detecting said PCR amplicon;
wherein the presence of said PCR amplicon indicates a positive diagnosis of IPA.

9. The quantitative PCR method of claim 8 wherein said patient sample is bronchoalveolar lavage (BAL) fluid.

10. The quantitative PCR method of claim 9 wherein said *Aspergillus* spp. gene is a ribosomal RNA (rRNA) gene.

11. The quantitative PCR method of claim 10 wherein said rRNA gene is an 18S rRNA gene.

12. The quantitative PCR method of claim 11 wherein said 18S rRNA gene comprises the nucleotide sequence (SEQ ID NO: 6).

13. The quantitative PCR method of claim 12 wherein said primer set comprises a forward primer comprising the nucleotide sequence 5'-GAT AAC GAA CGA GAC CTC GG-3' (SEQ ID NO: 1) and a reverse primer 5'-AGA CCT GTT ATT GCC GCG C-3' (SEQ ID NO: 2).

14. The quantitative PCR method of claim 13 wherein the step of detecting said PCR amplicon comprises the step of hybridizing a probe comprising the nucleotide sequence 5'-FAM CTT AAA TAG CCC GGT CCG C BHQ-3' (SEQ ID NO: 5).

* * * * *

SEQUENCE LISTING

<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
gataacgaac gagacctcgg                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
agacctgtta ttgccgcgc                                               19

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
gcctggtgca aaaattgctt atc                                          23

<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 4
ctaagacaag tgtgtttatg gtattg                                       26

<210> SEQ ID NO 5
<211> LENGTH: 19
<212> TYPE: DNA
<213> ORGANISM: Artificial Sequence
<220> FEATURE:
<223> OTHER INFORMATION: Artificial Sequence

<400> SEQUENCE: 5
cttaaatagc ccggtccgc                                               19

<210> SEQ ID NO 6
<211> LENGTH: 1798
<212> TYPE: DNA

<213> ORGANISM: Artificial Sequence
<220> FEATURE:
<223> OTHER INFORMATION: Synthetic oligonucleotide

<400> SEQUENCE: 6

```
aacctggttg atcctgccag tagtcatatg cttgtctcaa agattaagcc atgcatgtct        60
aagtataagc aatttatacg gtgaaactgc gaatggctca ttaaatcagt tatcgtttat       120
ttgatagtac cttactacat ggatacctgt ggtaattcta gagctaatac atgctaaaaa       180
cctcgacttc ggaaggggtg tatttattag ataaaaaacc aatgcccttc ggggctcctt       240
ggtgaatcat aataacttaa cgaatcgcat ggccttgcgc cggcgatggt tcattcaaat       300
ttctgcccta tcaactttcg atggtaggat agtggcctac catggtggca acgggtaacg       360
gggaattagg gttcgattcc ggagagggag cctgagaaac ggctaccaca tccaaggaag       420
gcagcaggcg cgcaaattac ccaatcccga cacggggagg tagtgacaat aaatactgat       480
acggggctct tttgggtctc gtaattggaa tgagtacaat ctaaatccct taacgaggaa       540
caattggagg gcaagtctgg tgccagcagc cgcggtaatt ccagctccaa tagcgtatat       600
taaagttgtt gcagttaaaa agctcgtagt tgaaccttgg gtctggctgg ccggtccgcc       660
tcaccgcgag tactggtccg gctggacctt tccttctggg gaacctcatg gccttcactg       720
gctgtggggg gaaccaggac ttttactgtg aaaaaattag agtgttcaaa gcaggccttt       780
gctcgaatac attagcatgg aataatagaa taggacgtgc ggttctattt tgttggtttc       840
taggaccgcc gtaatgatta atagggatag tcggggcgt cagtattcag ctgtcagagg       900
tgaaattctt ggatttgctg aagactaact actgcgaaag cattcgccaa ggatgttttc       960
attaatcagg gaacgaaagt tagggatcg aagacgatca gataccgtcg tagtcttaac      1020
cataaactat gccgactagg gatcgggcgg tgtttctatg atgacccgct cggcaccta       1080
cgagaaatca agttttttgg gttctggggg gagtatggtc gcaaggctga aacttaaaga      1140
aattgacgga agggcaccac aaggcgtgga gcctgcggct taatttgact caacacgggg      1200
aaactcacca ggtccagaca aaataaggat tgacagattg agagctcttt cttgatcttt      1260
tggatggtgg tgcatggccg ttcttagttg gtggagtgat ttgtctgctt aattgcgata      1320
acgaacgaga cctcggccct taaatagccc ggtccgcatt tgcgggccgc tggcttctta      1380
gggggactat cggctcaagc cgatggaagt gcgcggcaat aacaggtctg tgatgccctt      1440
agatgttctg ggccgcacgc gcgctacact gacagggcca gcgagtacat caccttggcc      1500
gagaggtctg ggtaatcttg ttaaaccctg tcgtgctggg gatagagcat tgcaattatt      1560
gctcttcaac gaggaatgcc tagtaggcac gagtcatcag ctcgtgccga ttacgtccct      1620
gccctttgta cacaccgccc gtcgctacta ccgattgaat ggctcggtga ggccttcgga      1680
ctggctcagg ggagttggca acgactcccc agagccggaa agttggtcaa acccggtcat      1740
ttagaggaag taaagtcgt aacaaggttt ccgtaggtga acctgcagaa ggatcaag         1798
```

<210> SEQ ID NO 7
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 7

```
gcctggtgca aaaattgctt atcaaattga acggtcaatt ggaagtggcg gaagaacagc        60
tattgcaaac gccatcgcac aataccataa acacacttgt cttag                      105
```

```
<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 8
cttccgccac ttccaattga ccgttca                                        27

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ctcttagctg agtgtcccgc                                                20

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 10
cttaatcatg gcctcagttc cga                                            23

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
ccgagccgcc tggataccgc agcta                                          25

<210> SEQ ID NO 12
<211> LENGTH: 45
<212> TYPE: DNA
<213> ORGANISM: Aspergillus clavatus

<400> SEQUENCE: 12
cgaaaacgaa cgagacctcg gcccttaaat agcccggtcc gcatt                    45

<210> SEQ ID NO 13
<211> LENGTH: 45
<212> TYPE: DNA
<213> ORGANISM: Aspergillus fischerianus

<400> SEQUENCE: 13
cgataacgaa cgagacctcg gcccttaaat agcccggtcc gcatt                    45

<210> SEQ ID NO 14
<211> LENGTH: 45
<212> TYPE: DNA
<213> ORGANISM: Aspergillus flavus

<400> SEQUENCE: 14
cgataacgaa cgagacctcg gcccttaaat agcccggtcc gcgtt                    45

<210> SEQ ID NO 15
```

```
<211> LENGTH: 45
<212> TYPE: DNA
<213> ORGANISM: Aspergillus fumigatus

<400> SEQUENCE: 15
cgataacgaa cgagacctcg gcccttaaat agcccggtcc gcatt            45

<210> SEQ ID NO 16
<211> LENGTH: 45
<212> TYPE: DNA
<213> ORGANISM: Aspergillus nidulans

<400> SEQUENCE: 16
cgataacgaa cgagacctcg gcccttaaat agcccggtcc gcgtc            45

<210> SEQ ID NO 17
<211> LENGTH: 45
<212> TYPE: DNA
<213> ORGANISM: Aspergillus oryzae

<400> SEQUENCE: 17
cgataacgaa cgagacctcg gcccttaaat agcccggtcc gcgtt            45

<210> SEQ ID NO 18
<211> LENGTH: 45
<212> TYPE: DNA
<213> ORGANISM: Aspergillus terreus

<400> SEQUENCE: 18
cgataacgaa cgagacctcg gcccttaaat agcccggtcc gcatt            45

<210> SEQ ID NO 19
<211> LENGTH: 45
<212> TYPE: DNA
<213> ORGANISM: Aspergillus ustus

<400> SEQUENCE: 19
cgataacgaa cgagacctcg gcccttaaat agcccggtcc gcgtc            45

<210> SEQ ID NO 20
<211> LENGTH: 45
<212> TYPE: DNA
<213> ORGANISM: Paecilomyces variotii

<400> SEQUENCE: 20
cgataacgaa cgagacctcg gcccttaaat agcccggtcc gcgtt            45

<210> SEQ ID NO 21
<211> LENGTH: 45
<212> TYPE: DNA
<213> ORGANISM: Penicillium chrysogenum

<400> SEQUENCE: 21
cgataacgaa cgagacctcg gcccttaaat agcccggtcc gcatt            45

<210> SEQ ID NO 22
<211> LENGTH: 46
<212> TYPE: DNA
<213> ORGANISM: Candida albicans

<400> SEQUENCE: 22
cgataacgaa cgagacctta acctactaaa tagtgctgct agcatt           46

<210> SEQ ID NO 23
```

```
<211> LENGTH: 46
<212> TYPE: DNA
<213> ORGANISM: Saccharomyces cerevisiae

<400> SEQUENCE: 23
cgataacgaa cgagacctta acctactaaa tagtggtgct agcatt            46

<210> SEQ ID NO 24
<211> LENGTH: 49
<212> TYPE: DNA
<213> ORGANISM: Homo sapiens

<400> SEQUENCE: 24
cgataacgaa cgagactctg gcatgctaac tagttacgcg acccccgag         49

<210> SEQ ID NO 25
<211> LENGTH: 23
<212> TYPE: DNA
<213> ORGANISM: Aspergillus clavatus

<400> SEQUENCE: 25
tgcgcggcaa taacaggtct gtc                                     23

<210> SEQ ID NO 26
<211> LENGTH: 23
<212> TYPE: DNA
<213> ORGANISM: Aspergillus fischerianus

<400> SEQUENCE: 26
tgcgcggcaa taacaggtct gtc                                     23

<210> SEQ ID NO 27
<211> LENGTH: 23
<212> TYPE: DNA
<213> ORGANISM: Aspergillus flavus

<400> SEQUENCE: 27
tgcgcggcaa taacaggtct gtc                                     23

<210> SEQ ID NO 28
<211> LENGTH: 23
<212> TYPE: DNA
<213> ORGANISM: Aspergillus fumigatus

<400> SEQUENCE: 28
tgcgcggcaa taacaggtct gtc                                     23

<210> SEQ ID NO 29
<211> LENGTH: 23
<212> TYPE: DNA
<213> ORGANISM: Aspergillus nidulans

<400> SEQUENCE: 29
tgcgcggcaa taacaggtct gtc                                     23

<210> SEQ ID NO 30
<211> LENGTH: 23
<212> TYPE: DNA
<213> ORGANISM: Aspergillus oryzae

<400> SEQUENCE: 30
tgcgcggcaa taacaggtct gtc                                     23

<210> SEQ ID NO 31
```

```
<211> LENGTH: 23
<212> TYPE: DNA
<213> ORGANISM: Aspergillus terreus

<400> SEQUENCE: 31
tgcgcggcaa taacaggtct gtc                                          23

<210> SEQ ID NO 32
<211> LENGTH: 23
<212> TYPE: DNA
<213> ORGANISM: Aspergillus ustus

<400> SEQUENCE: 32
tgcgcggcaa taacaggtct gtc                                          23

<210> SEQ ID NO 33
<211> LENGTH: 23
<212> TYPE: DNA
<213> ORGANISM: Paecilomyces variotii

<400> SEQUENCE: 33
tgcgcggcaa taacaggtct gtc                                          23

<210> SEQ ID NO 34
<211> LENGTH: 23
<212> TYPE: DNA
<213> ORGANISM: Penicillium chrysogenum

<400> SEQUENCE: 34
tgcgcggcaa taacaggtct gtc                                          23

<210> SEQ ID NO 35
<211> LENGTH: 23
<212> TYPE: DNA
<213> ORGANISM: Candida albicans

<400> SEQUENCE: 35
tttgaggcaa taacaggtct gtc                                          23

<210> SEQ ID NO 36
<211> LENGTH: 23
<212> TYPE: DNA
<213> ORGANISM: Saccharomyces cerevisiae

<400> SEQUENCE: 36
tttgaggcaa taacaggtct gtc                                          23

<210> SEQ ID NO 37
<211> LENGTH: 22
<212> TYPE: DNA
<213> ORGANISM: Homo sapiens

<400> SEQUENCE: 37
attgagcaat aacaggtctg tc                                           22
```